US011001797B2

(12) United States Patent
Domansky et al.

(10) Patent No.: US 11,001,797 B2
(45) Date of Patent: May 11, 2021

(54) DEVICES AND METHODS FOR IN VITRO AEROSOL DELIVERY

(71) Applicant: PRESIDENT AND FELLOWS OF HARVARD COLLEGE, Cambridge, MA (US)

(72) Inventors: Karel Domansky, Charlestown, MA (US); Michael Karpelson, Cambridge, MA (US); Donald E. Ingber, Boston, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 884 days.

(21) Appl. No.: 14/391,995

(22) PCT Filed: Apr. 15, 2013

(86) PCT No.: PCT/US2013/036569
§ 371 (c)(1),
(2) Date: Oct. 10, 2014

(87) PCT Pub. No.: WO2013/155513
PCT Pub. Date: Oct. 17, 2013

(65) Prior Publication Data
US 2015/0079670 A1    Mar. 19, 2015

Related U.S. Application Data

(60) Provisional application No. 61/623,893, filed on Apr. 13, 2012.

(51) Int. Cl.
*C12M 1/00*    (2006.01)
*A61M 11/00*    (2006.01)
*B05B 11/00*    (2006.01)

(52) U.S. Cl.
CPC .......... *C12M 29/06* (2013.01); *A61M 11/005* (2013.01); *B05B 11/3028* (2013.01); *A61M 2205/0244* (2013.01)

(58) Field of Classification Search
CPC ................ C12M 29/06; A61M 11/005; A61M 2205/0244; B05B 11/3028; B41J 2/14201; B41J 2/1607; B41J 2/1632
See application file for complete search history.

(56) References Cited

U.S. PATENT DOCUMENTS

| 4,857,464 A | * | 8/1989 | Weathers ............... C12M 21/08 435/289.1 |
| 6,530,370 B1 | | 3/2003 | Heinonen |

(Continued)

FOREIGN PATENT DOCUMENTS

WO    WO-2005107946 A2 *  11/2005    ............ B01L 3/0268

OTHER PUBLICATIONS

English Translation of WO2005/107946 Accessed Jan. 2019 (Year: 2019).*

*Primary Examiner* — William H. Beisner
*Assistant Examiner* — Danielle B Henkel
(74) *Attorney, Agent, or Firm* — Nixon Peabody LLP

(57) ABSTRACT

A system and methods for aerosol delivery of an entity or agent are disclosed. The system and methods can include a target application surface. A nebulizer can be located in close proximity to the target application surface. The nebulizer can include a chamber to hold the entity, a nozzle plate including one nozzle, and a piezoelectric element coupled to the nozzle plate. A power source can be coupled to the piezoelectric element. The power source, when activated, can energize the piezoelectric element to vibrate the nozzle plate to cause the entity to be nebulized through the nozzle to impact the target application surface.

9 Claims, 20 Drawing Sheets

CROSS-SECTION 8A-8A'

(56) References Cited

U.S. PATENT DOCUMENTS

| | | | |
|---|---|---|---|
| 2002/0129813 A1 | 9/2002 | Litherland et al. | |
| 2005/0116992 A1* | 6/2005 | Akahane | B41J 2/1612 347/54 |
| 2005/0273995 A1 | 12/2005 | Kanagasabapathi et al. | |
| 2009/0134235 A1 | 5/2009 | Ivri | |
| 2010/0186524 A1* | 7/2010 | Ariessohn | G01N 1/2202 73/863.22 |
| 2010/0302322 A1* | 12/2010 | Wang | B41J 2/14201 347/68 |
| 2011/0000482 A1 | 1/2011 | Gumaste et al. | |
| 2014/0158233 A1* | 6/2014 | Leslie | C12M 29/00 137/561 R |
| 2014/0329300 A1* | 11/2014 | Lundt | G01N 1/31 435/287.2 |
| 2014/0342445 A1* | 11/2014 | Ingber | C12M 23/16 435/294.1 |

\* cited by examiner

TOP VIEW

CROSS-SECTION 10A-10A'

TOP VIEW

CROSS-SECTION 10C-10C'

TOP VIEW

CROSS-SECTION 11A-11A'

TOP VIEW

CROSS-SECTION 11C-11C'

TOP VIEW

CROSS-SECTION 12A-12A'

SCANNING

VIBRATING NOZZLE PLATE

ANNULAR PIEZOELECTRIC ELEMENT WITH ELECTRODES

TOP VIEW

FIG. 13A

ROBOTIC ARM *830*

*1310* ENTITY TO BE NEBULIZED

ELECTRICAL CONNECTIONS

WELL *814*

TRANSWELL INSERTS *822*

NEBULIZED ENTITY *1314*

*824* CELLS AT AIR-LIQUID INTERFACE

*820* CELL CULTURE MEDIUM

CROSS-SECTION 13A-13A'

FIG. 13B

DEVICES AND METHODS FOR IN VITRO AEROSOL DELIVERY

CROSS REFERENCE TO RELATED APPLICATIONS

This Application is a 35 U.S.C. § 371 National Phase Entry Application of International Application No. PCT/US2013/036569 filed Apr. 15, 2013, which designates the U.S., and which claims the benefit under 35 U.S.C. § 119(e) of U.S. Provisional Application No. 61/623,893 filed Apr. 13, 2012, the contents of each of which are incorporated herein by reference in their entirety.

GOVERNMENT SUPPORT

This invention was made with government support under grant no. U01-NS073474-01 awarded by the National Institutes of Health. The U. S. government has certain rights in the invention.

TECHNICAL FIELD

This disclosure relates to devices and methods for aerosol delivery. More specifically, the disclosure relates to a nebulizer system having one or more piezoelectric elements and a nozzle plate for aerosol delivery to a target location. The target location can include biologic material, such as cells cultured in a channel of a microfluidic device.

BACKGROUND

Many drugs appear promising in animal studies but fail in human clinical trials. This presents a need to substitute or complement animal studies with in vitro models capable of reconstituting the key structural and mechanical features of whole organs. While in vitro microfluidic models have been developed to capture the relevant features of whole organs, drugs need to be delivered to the cells without perturbing the air-liquid interface in order to study cell response to drugs in such models. Generally, an aerosol is generated off-chip, e.g., with a commercial nebulizer and then is delivered to cells inside the microfluidic model. However, in order to increase deposition efficiency and/or allow more accurate and localized dosing, devices and methods that allow liquid micro-droplets or solid particles to be generated on-chip and delivered from the micro-channel ceiling in on-demand fashion are in need.

In vitro cell culture has been traditionally performed with fully submerged cells, where an active agent to be investigated is added to the cell culture medium completely covering the cells. For primary contact organs such as lung, nose, oropharynx, skin, or eye, this represents an unrealistic way of exposure, since the in vivo exposure occurs at the air-liquid interface. Thus, in vitro culture of primary cells or cell lines derived from these organs at the air-liquid interface coupled with direct exposure to nebulized entities of interest better mimics physiological conditions.

A number of systems for exposing cells at the air-liquid interface to nebulized entities have been previously utilized. Such systems rely mainly on deposition by gravitational settling, convection and diffusion, inertial impaction, and electrostatic forces. In these systems, depending on the type of solid particle or liquid droplet generation desired, nebulization is performed by different means including spark discharge generators, dry powder inhalers, pneumatic nebulizers, and vibrating mesh nebulizers. Commercially available systems for studying the effects of airborne substances on cells cultured at air-liquid interface are for example available from VITROCELL Systems GmbH and Cultex Laboratories GmbH.

Because entities in these systems are nebulized in generators that typically require a relatively large air flow rate for their optimum performance (e.g., pneumatic nebulizers) and delivered to a chamber containing the cells over a long path by a pump, deposition suffers from low efficiency. For example, deposition efficiency of a system for exposing cells to ultrafine carbonaceous particles was 2%. Higher deposition efficiencies of 15-30% are achieved for depositing charged nanoparticles using electrostatic forces. However, the deposition efficiency values are upper limits for the overall deposition efficiency as they do not account for additional losses due to, for example, residual mass in particle generator, losses in the transport lines and waste of material during the transient turn-on/turn-off cycles of the deposition.

Direct consequences of low deposition efficiency include increased cost, in particular when more expensive compounds are used. Because the exposure systems are frequently used to investigate the effects of toxic compounds on cells, low deposition efficiency results in generation of a large volume of air that represents a hazard to personnel operating the system. Also the air must be disposed as toxic chemical waste requiring employing expensive scrubbers to comply with toxic chemical waste disposal regulations.

Another consequence of low deposition efficiency is more difficult determination of the deposited dose as the deposited dose cannot be simply implied by measuring the loss of mass of source material in the nebulizer. Only the more recent exposure systems contain real time monitoring sensors of the deposited dose. Typically, such systems use a quartz crystal microbalance sensor placed instead of cells into the deposition chamber. Such sensors add to the complexity of the system.

One approach for increasing overall deposition efficiency is to use nebulizers that have low residual volume, short turn-on/turn-off time and do not rely on nebulization by airflow. Nebulizers based on vibrating mesh technology meet these requirements and have been used for delivering aerosol to humans, animals, and cells inside cell culture systems. While vibrating mesh nebulizers have been used as a source/or generator of aerosol for cells cultured at the air-liquid interface, vibrating mesh nebulizer was required to be used in combination with a pumping device to deliver the aerosol to the cells from a high position.

Piezoelectric droplet ejectors have been used in commercial nebulizers for pulmonary drug delivery. In these nebulizers, aerosol is generated with a plate containing an array of nozzles. The nozzle plate is vibrated at frequencies typically between 100 and 200 kHz either actively with an annular piezoelectric element surrounding the nozzle plate or passively by vibrating horn transducer generating vibrations that are transmitted to the nozzle plate through a liquid medium. Vibrations of the nozzle plate result in expulsion liquid through the nozzles in form of fine droplets. Examples of commercial products employing vibrating mesh technology include Aerogen Aeroneb nebulizers with OnQ™ Aerosol Generator, Omron NE-U22V MicroAir VM nebulizers, PARI Pharma GmbH eFlow® Trio® nebulizers or Beurer IHSO nebulizers. Aerosol generated by vibrating mesh is characterized by fine droplet fraction, narrow droplet size distribution and low velocity. For example, Aerogen sells vibrating mesh nebulizer AeronebLab with droplet median diameter of 2.5-4.0 µm. However, these existing nebulizers cannot be used for close-proximity delivery of an active agent to a target, e.g., a cell in vitro without disturbing air-liquid interface as described herein, because the existing piezoelectric droplet ejectors are configured and constructed to be used in combination with a pump for delivering the aerosol from a high position (e.g., ~100 mm-200 mm) to large surface area, e.g., by cloud settling, at a high flow rate, thus resulting in a very low deposition efficiency (e.g., about 7.2% efficiency).

The generated aerosol in current nebulizers requires delivery by a pump, for example at a flow rate of 5 L/min to a 20-L deposition chamber. Therefore, the droplets are deposited on cells by cloud settling from approximately 200 mm in height. The overall deposition efficiency for exposing cells on Transwell® inserts in two six well plates was found to be 7.2% using such a nebulizer. Accordingly, there are no existing in vitro aerosol delivery devices that can allow an active agent to be nebulized a short distance (e.g., from hundreds of microns to several millimeters) directly above the cells at an air-liquid interface. Thus, there is a need to develop novel devices and methods that can be used for in vitro aerosol delivery with higher deposition efficiency and thus decrease the cost of disposing hazardous aerosols.

SUMMARY

Embodiments of various aspects described herein relate to nebulizers, systems and methods for aerosol delivery of at least one entity. The nebulizers, systems, and methods described herein can be used to deliver an aerosol of at least one entity (e.g., but not limited to any active agent such as proteins, peptides, polynucleotides, oligonucleotides (e.g., siRNAs, and gene vectors), drugs or therapeutic agents, small molecules, cells, viruses, monomers, polymers, or any combinations thereof; reagents such as cell labeling dyes and/or fluorescent dyes; solid particles such as quantum dots, magnetic particles, and/or non-magnetic particles) to any target surface (e.g., a surface of an in vitro cell culture device or a cell monolayer cultured therein), and/or to form particles (e.g., nanoparticles or microparticles) comprising the entity. The nebulizers described herein generally comprise a chamber to hold a dose of at least one entity (an agent chamber), a nozzle plate including at least one nozzle, and a piezoelectric element permanently or detachably coupled to the nozzle plate. The entity loaded into the agent chamber can be in a form of a solution, a suspension, powder, particulates, or particles small enough to be ejected through the nozzles. Unlike the existing low-efficient nebulizers, which are generally constructed to be used in combination with a pump to deliver an aerosol from a high position (e.g., ~100 mm-~200 mm) to a large surface, e.g., by cloud setting, the nebulizers described herein can be used in close proximity (e.g., a few hundred microns) to a target surface (e.g., a cell monolayer) without the use of a pump, thus enabling more efficient deposition of an entity.

In one aspect, the system for aerosol delivery of at least one entity comprises (a) a nebulizer including a chamber to hold a dose of the entity (termed as an agent chamber herein), a nozzle plate including at least one nozzle, and a piezoelectric element coupled to the nozzle plate; and a power source coupled to the piezoelectric element, the power source, when activated, energizing the piezoelectric element to vibrate the nozzle plate to cause the dose of the entity to be nebulized through the nozzle in a predefined direction. The nozzle plate forms the bottom end of the agent chamber. The piezoelectric element can be directly or indirectly coupled to the nozzle plate. For example, in one embodiment, the piezoelectric element can be attached to a support film or beam that can induce vibrations in the nozzle plate, thus generating an aerosol of the entity.

The nebulizers described herein can be integrated with any device or system to deposit at least one entity onto a target surface therein. In some embodiments, the nebulizers described herein can be integrated with an in vitro cell culture device, e.g., a multi-well cell culture plate or chamber, or a microfluidic device, e.g., an organ-on-chip device. Accordingly, systems for providing a nebulized entity to a cell in an in vitro culture system are also provided herein. For example, in one aspect, the system directed to use in a cell culture plate comprises (i) a plate including at least one well; (ii) an insert holding cells, the insert suspended in the well; (iii) a nebulizer in close proximity to the insert, the nebulizer including a chamber adapted to hold the entity, a nozzle plate including at least one nozzle, and a piezoelectric element coupled to the nozzle plate; and (iv) a power source coupled to the piezoelectric element, the power source, when activated, energizing the piezoelectric element to vibrate the nozzle plate and cause the entity to be nebulized through the nozzle forming an aerosol that is applied cells in the insert.

In another aspect, the system directed to use in a microfluidic device comprises (i) at least one microfluidic device comprising a channel; (ii) a nebulizer in close proximity to the channel, the nebulizer including a chamber adapted to hold the entity, a nozzle plate including at least one nozzle, and a piezoelectric element capable of coupling to the nozzle plate; and (iii) a power source coupled to the piezoelectric element, the power source, when activated, energizing the piezoelectric element to vibrate the nozzle plate and cause the entity to be nebulized through the nozzle forming an aerosol that is delivered to the channel of the microfluidic device. In some embodiments, the nozzles in the nozzle plate can be configured to space apart by a distance such that multiple entities delivered via respective nozzles can be deposited onto spatially-distinct target areas of a single channel within the microfluidic device, thus permitting multiplexing (e.g., simultaneous detection of cell responses to each of a plurality of entities in a single system).

Methods for using the nebulizers and/or systems described herein are also provided. For example, a method for producing an aerosol of an entity comprises energizing the piezoelectric element of the nebulizer to vibrate the nozzle plate and cause the entity loaded in the agent chamber of the nebulizer to be nebulized through the nozzle forming an aerosol.

In some embodiments, the method can further comprise positioning the nebulizer in close proximity to a target surface desired to be deposited with the entity such that the aerosol of the entity ejected from the nozzle can be deposited on the target surface.

The foregoing and additional aspects and implementations of the present disclosure will be apparent to those of ordinary skill in the art in view of the detailed description of various embodiments and/or aspects, which is made with reference to the drawings, a brief description of which is provided next.

BRIEF DESCRIPTION OF THE DRAWINGS

FIG. 13A is a top view of a nebulizer having a single nozzle used in the system shown in FIG. 8A-8B for localized aerosol deposition;

FIG. 13B is a side view of the nebulizer in FIG. 13A taken from the line 13A-13A' in FIG. 13A.

DETAILED DESCRIPTION

The present invention relates to devices and methods for aerosol delivery of at least one entity or agent to a target. In some examples below, the devices and methods can be used for aerosol delivery of at least one entity or agent to a cell in vitro. The integration of one or more vibrating nozzle plates into microfluidic devices can generate aerosols on-system or on-device (e.g., on-chip) and in close proximity to a target (e.g., cells) or a surface that enables accurate deposition or dosing and localized aerosol deposition. In some embodiments, the agent can include a drug or drug formulation and the nebulizers described herein can be used for nebulizing drugs in solution, suspension or powder. They can also be used for nebulizing fragile or labile molecules such as proteins and peptides, as well as living viruses or cells, without significant heating or degradation. Furthermore, because small amounts of solutions or powders are used with minimal or virtually zero remaining waste, toxic compounds can be tested with lowered risk hazards.

In one aspect of the invention provided herein is a nebulizer comprising an agent chamber to hold one or more agents to be nebulized; a nozzle plate enclosing the bottom of the agent chamber; and a piezoelectric element adapted to induce vibration in the nozzle plate. The agent chamber comprises at least one or more compartments with the bottom enclosed by the nozzle plate. The nozzle plate comprises one or more nozzles. The piezoelectric element comprises an aperture to permit flow of the entity (or entities) from the compartment(s) though the nozzles in the plate.

Figure 1:
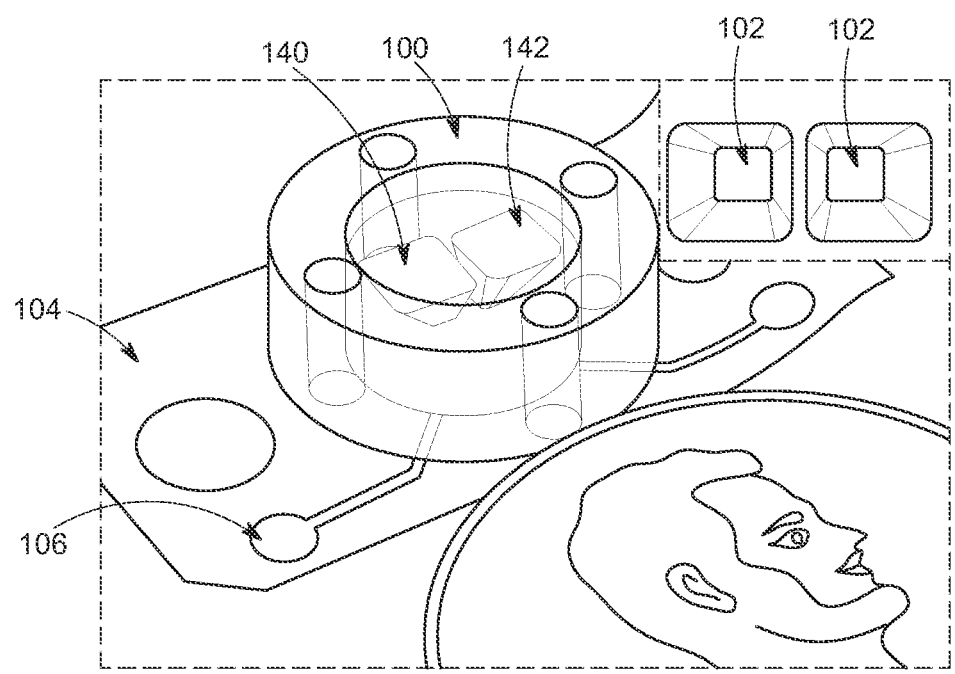
FIG. 1 is a perspective view showing an exemplary vibrating mesh nebulizer with a dual medication chamber.
Figures 2A, 2B:
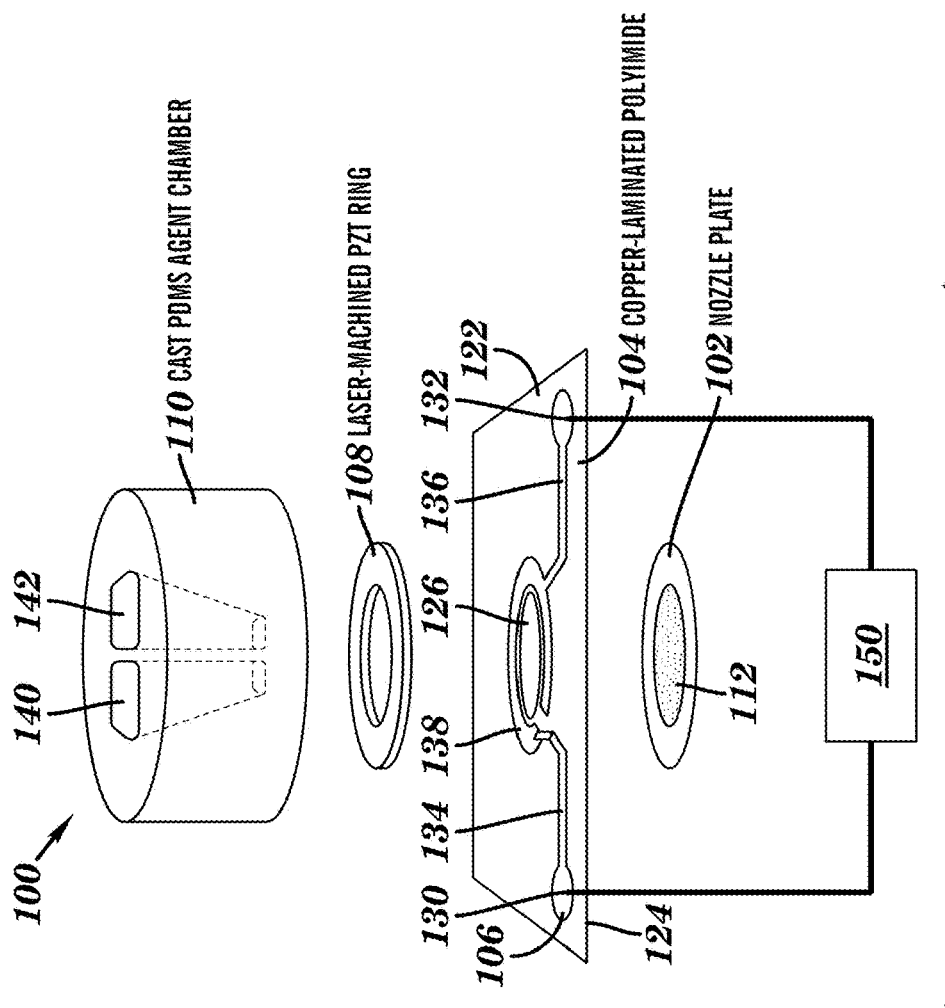
FIG. 2A is an exploded schematic diagram of the exemplary nebulizer in FIG. 1.
FIG. 2B is a side view schematic diagram of the exemplary nebulizer in FIG. 1.

FIG. 1 is a perspective view showing an exemplary vibrating mesh nebulizer 100 which is located in proximity to a target application surface. FIG. 2A is an exploded perspective view of the components of the nebulizer 100 and FIG. 2B is a side perspective view of the nebulizer 100. The vibrating mesh nebulizer 100 includes a nozzle plate 102, a support film 104, an electrode layer 106, a piezoelectric element 108 and an agent chamber 110. The nebulizer 100 allows for aerosol delivery of a predefined quantity of an entity (e.g., an active agent) to a target application surface. As will be explained below, positioning the nozzle plate 102 in close proximity (e.g., hundreds of microns or more) above a target application surface can allow for localized deposition of one or more entities to the target area. In some embodiments, positioning the nozzle plate 102 in close proximity (e.g., hundreds of microns or more) above a target application surface having cells disposed thereon can allow for localized deposition of one or more entities (e.g., one or more active agents) to the cells. In some embodiments, the nebulizer can be used for molecule or cell seeding, e.g., depositing molecules or cells on a target surface or on a cell layer.

The nozzle plate 102 forms the bottom of an agent chamber 110 and comprises one or more nozzles depending on surface area and/or number of positions to be deposited by the nebulizer 100. For example, the nozzle plate 102 can comprise one to 500 or more nozzles. In some embodiments, the nozzle place 102 can comprise at least 1, at least 2, at least 3, at least 5, at least 6, at least 7, at least 8, at least 9, at least 10, at least 25, at least 50, at least 100, at least 200, at least 300, at least 400, at least 500 or more nozzles. The nozzles can be arranged in any pattern in the plate 102, e.g., in an array, in a desired pattern, or in a random order. The arrangement of the nozzles can depend, in part, on a deposition pattern desired to be produced. In this example, the nozzle plate 102 includes at least approximately 300 nozzles 112 per agent chamber 110 arranged in a hexagonal pattern. In some embodiments where the agent chamber 110 comprises more than one compartment, the nozzle plate 102 can include at least about 300 nozzles 112 per compartment arranged in a hexagonal pattern. The number of nozzles 112 per agent chamber 110 or per compartment 140, 142 of the agent chamber 110 can range from 1 to the order of $10^6$.

In this example, the diameter of the nozzles 112 in the nozzle plate 102 approximately determines the size of the generated droplets or particles. Thus, the diameter of the nozzles 112 can be of any dimension, e.g., ranging from 1 nm to about 1000 µm, from about 500 nm to about 500 µm, or from about 1 µm to about 250 µm, or from about 5 µm to about 100 µm. In this example, the nozzle plate 102 includes the nozzles 112 which can include tapered holes with a size depending on the desired size of the generated microdroplets of the entity when the entity is nebulized. For example, the tapered holes forming the nozzles 112 can have a size of about 10-22 µm in diameter.

The nozzle plate 102 can be made of any suitable material and/or of any dimension or shape, depending on the applications and/or surface area to be deposited. For example, the nozzle plate 102 can be fabricated from metal, metal alloy, plastic, ceramic, and/or synthetic polymer. The nozzle plate 102 can be in a shape of a circle, a rectangle, a square, a polygon, or any irregular shape. The nozzle plate 102 can have a thickness of at least about 10 µm, at least about 20 µm, at least about 30 µm, at least about 40 µm, at least about 50 µm, at least about 60 µm, at least about 70 µm, at least about 80 µm, at least about 90 µm, at least about 100 µm, at least about 150 µm, at least about 300 µm or more. In some embodiments, the nozzle plate 102 can have a thickness of about 10 µm to about 1000 µm, or about 20 µm to about 500 µm, or about 30 µm to about 250 µm. The thickness of the nozzle plate 102 can be selected for tuning the average displacement of the nozzle plate 102 during vibration and thus the exit velocity of the droplets formed by the nebulizer 100. FIGS. 2A and 2B show a circular nozzle plate 102 fabricated from electroplated nickel having a thickness of 30-90 µm.

Figure 15A:
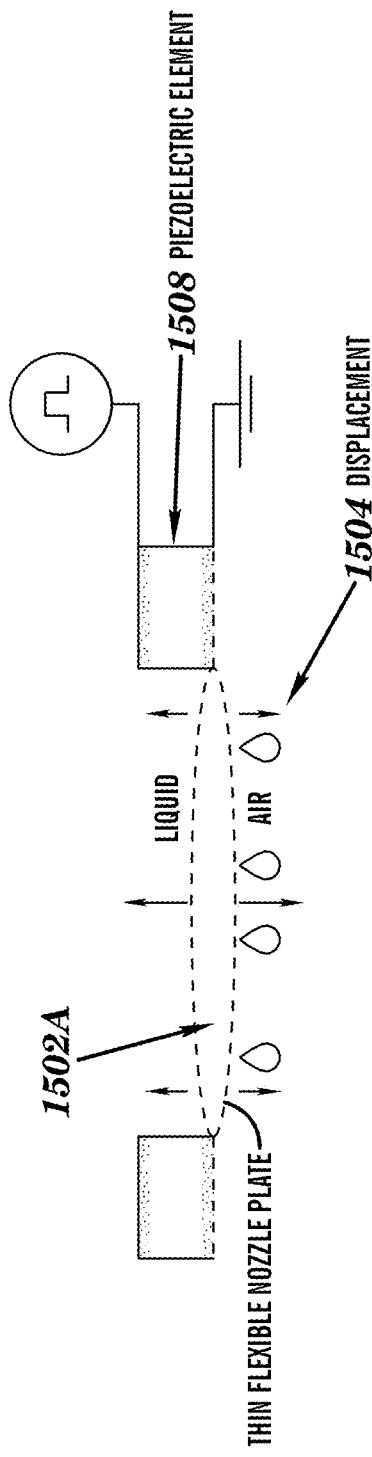
FIGS. 15A-15B are schematic diagrams showing principle of nebulization by flexible nozzle plate (FIG. 15A) and by rigid body motion (FIG. 15B).

In some embodiments of the invention, a nebulizer described herein can comprise a thin flexible nozzle plate 1502A with one or more nozzles and a piezoelectric element 1508A that is securely attached to the plate 1502A around the nozzles. In operation, an AC voltage signal can be applied to the electrodes of the piezoelectric element 1508 results in periodic deformations of the piezoelectric element 1508 and the propagation of vibrations in the nozzle plate 1502A. When there is a liquid above the nozzle plate 1502A and vibration conditions are set properly, vibrations of the nozzle plate result in ejection of droplets from the nozzles. Because, in this embodiment, the nozzle plate is rather thin and flexible, displacement 1504 (FIG. 15A) of the nozzles varies radially outward from the center of the piezoelectric element 1508. This can lead to variations in droplet velocity and/or size over the extent of the nozzle plate 1502A.

Figure 15B:
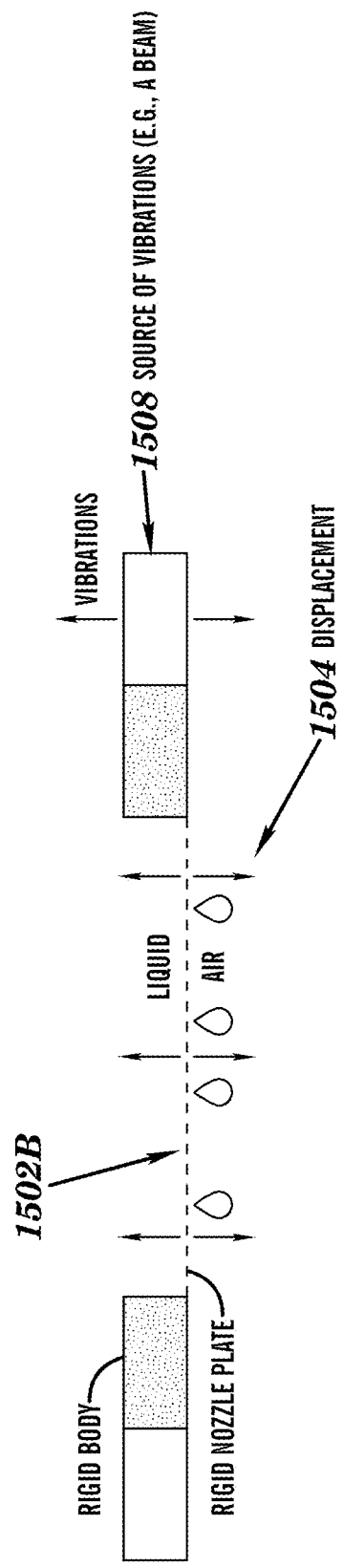

In alternative embodiments of the invention, as shown in FIG. 15B, a nebulizer can comprise a rigid nozzle plate 1502B with one or more nozzles and a piezoelectric element 1508B that is securely attached to the plate 1502B around the nozzles. It is based on motion of a rigid nozzle plate with one of more nozzles forming the bottom of an agent chamber. Because the agent chamber and the nozzle plate 1502B are rigid, the displacements of all nozzles in the plate 1502B are nearly identical over the extent of the nozzle plate 1502B, ensuring low variations in droplet velocity and/or size. An additional advantage of this arrangement is that agent chamber as described below can be a separate component that does not contain a piezoelectric element. As a result, it can be produced at a low cost and be made disposable.

Figure 16:
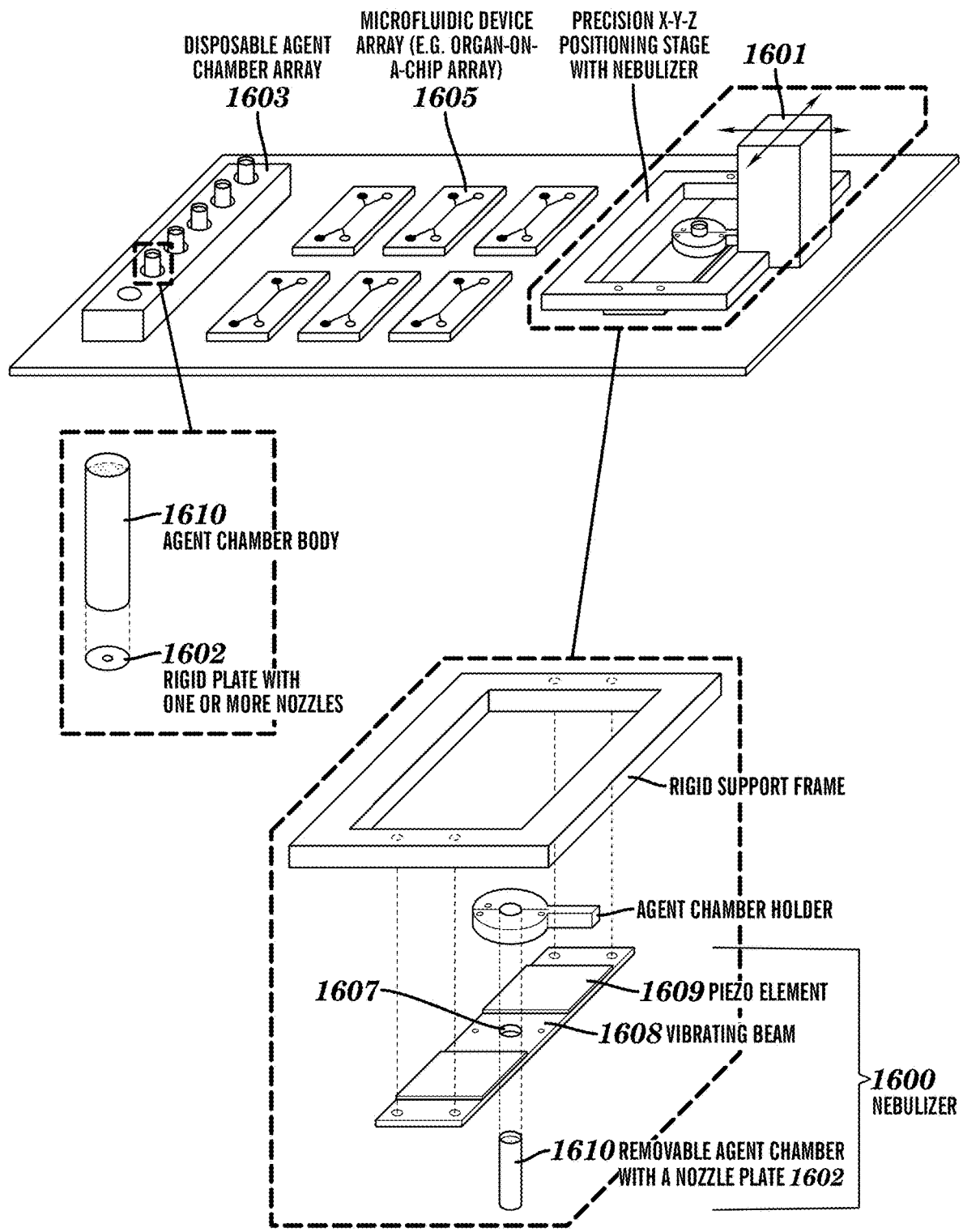
FIG. 16 is a diagrammatic view of a system utilizing one embodiment of a nebulizer (e.g., a nebulizer comprising a rigid nozzle plate) for aerosol delivery to an array of microfluidic devices, e.g., organs-on-chips.

The piezoelectric element 108 can be configured in any shape or form. For example, FIGS. 2A-2B shows a piezoelectric ring, while FIG. 16 shows a piezoelectric beam comprising a an aperture 1607 adapted to receive and carry an agent chamber 1610.

The piezoelectric element 108 can comprise one or more piezoelectric materials known in the art, including, e.g., but not limited to, quartz, antimony sulfoiodide, piezoelectric ceramic barium titanate, calcium barium titanate, lead titanate zirconates, TsTs-23, TsTBS-3, TsTSNV-1, PZT-5H, lead zirconate titanate (PZT), PZT-8, and/or any piezoceramic material. In some embodiments, as shown in FIGS. 2A-2B, the piezoelectric element 108 can be a piezoceramic ring (e.g., PZT ring), for example, laser-machined using commercially-available PSI-5H4E piezoceramic material from Piezo Systems Inc. (Woburn, Mass.).

The piezoelectric element 108 can be configured (e.g., by machining or laser-machining) to a certain dimension. In one embodiment, the dimension of the piezoelectric element 108 can be adapted to be fitted to an in vitro device (e.g., a cell culture device such as a microtiter plate, or a microfluidic device). FIGS. 2A-2B shows a piezoelectric element 108 (in a form of a ring) having a 127 µm thickness, a 2.5-mm inside diameter and a 5 mm outside diameter, but any suitable dimensions may be used. For example, in FIG. 16, rectangular piezoceramic elements 1609 with a thickness of 127 µm and dimensions of 10 mm by 13 mm are attached to a vibrating beam 1608 having a thickness of about 1 mm. The piezoelectric element 108 or 1609 may be coated with a metal such as being plated with Ni metallization.

In some embodiments where the piezoelectric element 108 is a thin ring, the piezoelectric element 108 can be attached to a support film or plate 104 (e.g., a polymeric film). A patterned electrode layer 106 can be formed on the polymeric film 104 and facilitate electrical contact with the piezoelectric element 108 during operation. In this example, the polymeric film 104 can include polyimide. The polymeric film 104 can have any shape and include a top surface 122 and a bottom surface 124. As shown in FIGS. 2A-2B, the polymeric film 104 can be a rectangular. The polymeric film 104 can include an aperture 126 through the film to allow transmission of aerosol to the nozzle plate 112 which can be mounted on the bottom surface 124.

The patterned electrode layer 106 can include a series of conductor paths on the top surface 122 of the polymeric film 104. The patterned electrode layer 106 can include two contacts 130 and 132 which can be coupled to a power source 150. The contacts 130 and 132 can be coupled to two traces 134 and 136 respectively which can be connected to a ring shaped conductor 138 which can provide electrical contact with the piezoelectric element 108. In this example, the electrode layer 106 can be patterned on the polymeric film 104 by any methods known in the art, including, for example, photolithography. The patterned electrode layer 106 can be made of any electrically-conducting material, including not limited to, copper, silicon, gold, titanium, platinum, and any other electrode material. The patterned electrode layer 106 allows pulses of electrical energy to actuate the piezoelectric element 108 causing the nozzle plate 102 to vibrate and thereby generating droplets of an agent carried in the agent chamber 110.

Figure 17:
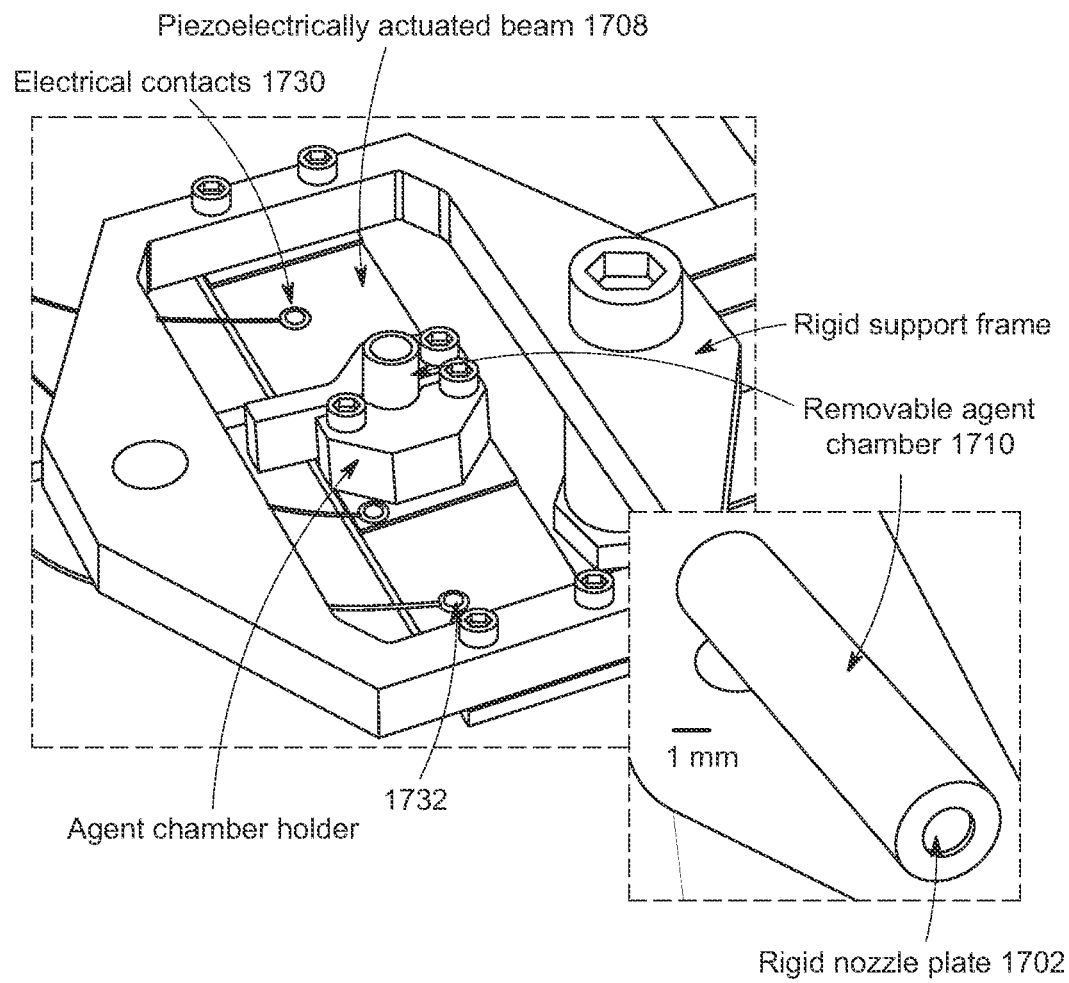
FIG. 17 is a photograph of an exemplary nebulizer comprising a rigid nozzle plate. Insert shows removable and disposable agent chamber comprising a nozzle plate at the bottom. The removable agent chamber is reversibly clamped to a piezoelectrically-actuated beam that is attached to a rigid frame. Diameter of the nozzles in the plate is approximately 10-μm.
Figure 18:
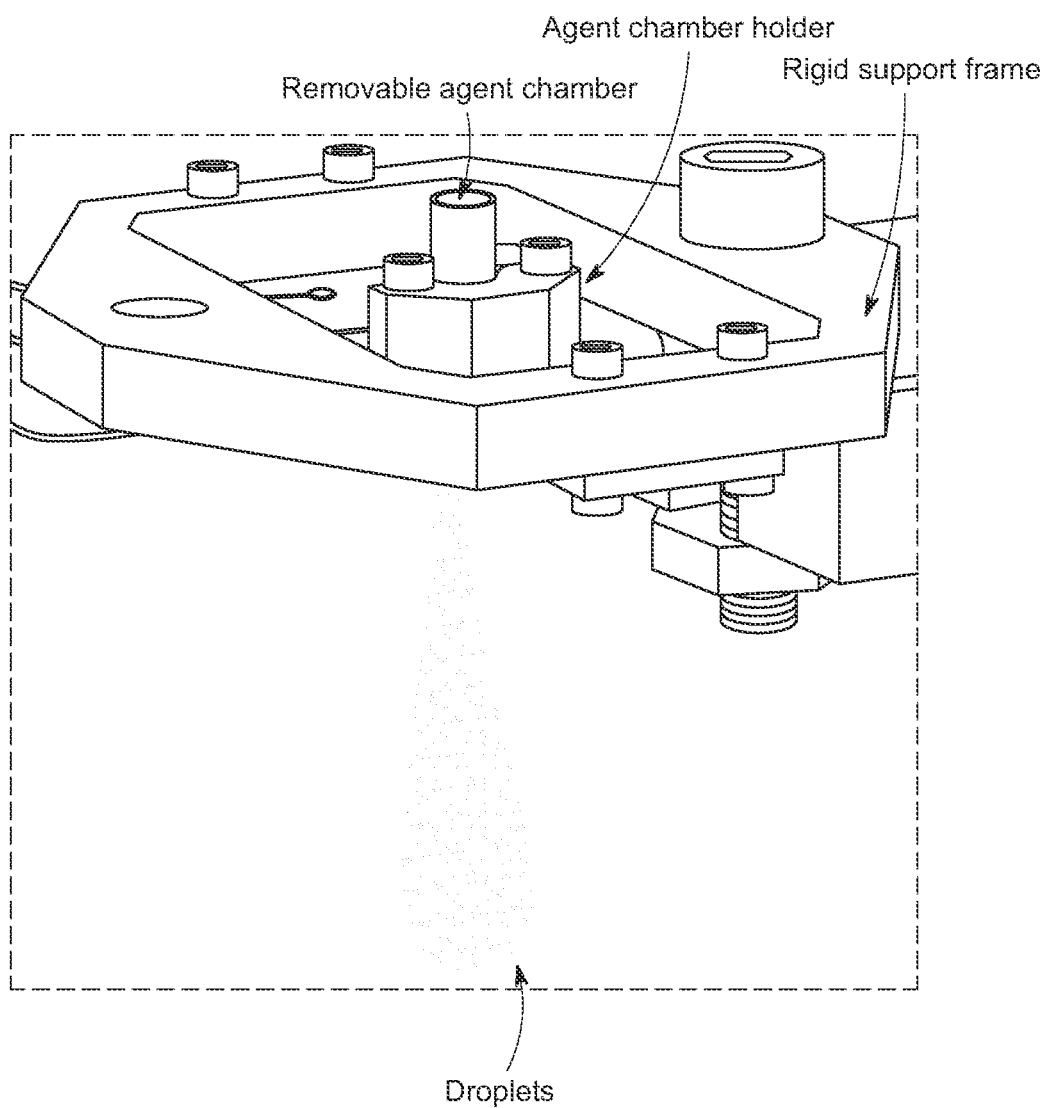
FIG. 18 is a photograph showing aerosol generation by the nebulizer shown in FIG. 17. Diameter of the nozzles in the plate is 22 μm. The beam was actuated approximately at 9 kHz. A plume of aerosol emanating from nozzle plate is visible under the nebulizer.

In some embodiments, the piezoelectric element can be attached to a rigid structure such that the rigid structure can be piezoelectrically-actuated and generate vibration. For example, as shown in FIGS. 16 and 17, a vibrating beam can be induced by energizing the piezoelectric element 1609 attached onto the rigid beam 1608 (piezoelectrically-actuated beam 1708) via electrode contacts 1730 and 1732 soldered onto the beam 1608 or 1708.

The agent chamber 110 can be shaped in any form and includes at least one or more compartments for containing one or more entities or agents (e.g., one or more active agents). For example, in FIGS. 2A-2B, the agent chamber 110 can be cylindrically shaped and include two (or more) compartments 140 and 142 having the bottom surface formed by the nozzle plate 102. FIG. 16 shows a cylindrically-shaped agent chamber 1610 with one compartment, wherein the bottom surface of the chamber is formed by the nozzle plate 1602. The compartments 140, 142, or 1610 allow fluid access to the nozzle plate 102, or 1608 through the aperture 107 or 1607 in the piezoelectric element 108 or 1608. The volume capacity of the compartments 140, 142 or 1610 can vary with a desired volume of agent to be deposited, and/or surface area to be deposited. Thus, the compartments 140, 142 or 1610 can have a volume capacity ranging from microliters to milliliters. For a microfluidic device, the volume capacity of the compartments 140 and 142 can, for example, range from 10 nL to about 1 mL, from about 50 nL to about 500 µL, from about 1 µL to about 250 µL, or from about 5 µL to about 100 µL. In accordance with some embodiments, for example, the agent chamber 110 in FIG. 1, each compartment 140 and 142 of the nebulizer 100 can have approx. 9 gt volume and approximately a 400 µm×400 µm bottom footprint. The compartments 140 and 142 can be separated by about 400 µm. In accordance with some embodiments, for example agent chamber 1610 or 1710 in FIG. 16 or 17, respectively, the single-compartment agent chamber 1610 or 1710 can have a volume capacity of about 20 µL. The compartments 140, 142 or 160 can be filled by pipetting liquids or dispensing solid powders into the compartments 140 and 142 in predefined amounts by volume or weight or molar concentration. The amount deposited in each compartment 140, 142 or 160 can be used to control and/or define the aerosol deposition amount or dose.

In accordance with the inventions described herein, attaching the compartmentalized chamber 110 or 1610 to the top of the nozzle plate 102 or 1610 in FIG. 1 or FIG. 16 does not impede vibrations of the nozzle plate 102 or 1610 or impact the function of the nebulizer 100 or 1600. Typically, any mass attached to the nozzle plate 102 or 1610 inside the piezoelectric element 108 or 1608 can dampen vibrations of the nozzle plate 102 or 1610 and interfere with aerosol generation. In particular, an agent chamber built from a hard material can prevent the device from nebulizing.

In accordance with some embodiments of the invention, the agent chamber 110 or 1610 can be fabricated from elastomeric materials and therefore does not interfere with the vibrations of the nozzle plate 102 or 1610. Examples of usable elastomeric materials include, but are not limited to, polydimethylsiloxane (PDMS), rubber, synthetic polyisoprene, polybutadiene, chloroprene rubber, polychloroprene, neoprene, baypren, butyl rubber (e.g., copolymer of isobutylene and isoprene), halogenated butyl rubbers (e.g., chloro butyl rubber; bromo butyl rubber), styrene-butadiene rubber (copolymer of styrene and butadiene), nitrile rubber (copolymer of butadiene and acrylonitrile), hydrogenated nitrile rubbers, ethylene propylene rubber, ethylene propylene diene rubber, epichlorohydrin rubber, polyacrylic rubber, silicone rubber, fluorosilicone rubber, fluoroelastomers, perfluoroelastomers, polyether block amides, chlorosulfonated polyethylene, ethylene-vinyl acetate, and any combinations thereof. FIGS. 2A and 2B shows an agent chamber fabricated from PDMS.

In FIGS. 2A-2B, the nebulizer 100 can be assembled by attaching the laser-machined PZT ring 108 with plated Ni metallization to the polyimide film 104. The patterned electrode layer 106 can be fabricated via photolithography to produce patterned copper electrodes in this example. Exemplary methods to fabricate the elastomeric agent chamber 110 with compartments 140 and 142 for aerosol delivery include, but are not limited to casting elastomers such as polydimethylsiloxane (PDMS) on top of the plasma activated nozzle plate assembly. A mold setup may be used that allows alignment of the nozzle plate 102 relative to the agent chamber 110. Another method is attaching laser-machined "Gel" layer (e.g., a polymer material available from Gel-Pak, Hayward, Calif.) (in the form of an agent chamber 110) to the nozzle plate 102.

Figure 3A:
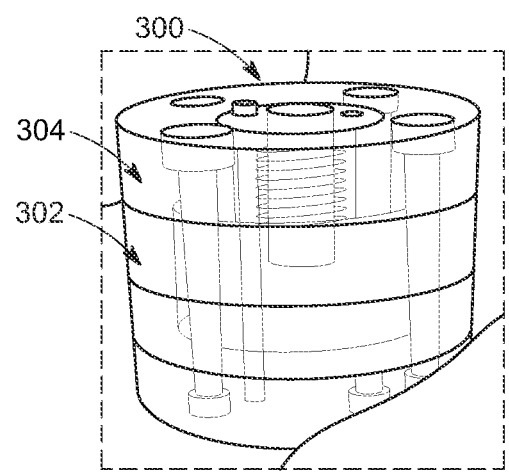
FIG. 3A is a perspective view of an exemplary mold assembly for casting the elastomeric medication chamber for the exemplary nebulizer in FIG. 1.
Figure 3B:
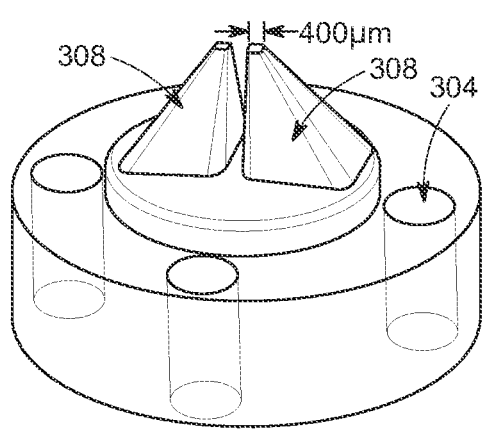
FIG. 3B is a perspective view of the mold insert of the mold assembly in FIG. 3A.

In some embodiments, the nozzle plate 102 can be bonded to or detachable from the bottom of the assembly of the piezoelectric element 108 and electrode layer 106, e.g., as shown in FIGS. 2A-2B. The agent chamber 110 may be cast on top of the assembly by using a mold assembly such as an acrylic mold, following plasma activation of the assembly. FIG. 3A shows a perspective view of an assembled mold 300 which can be placed on the film 104 to fabricate the agent chamber 110. The assembled mold 300 can include a mold 302 and a mold insert 304. The assembled mold 300 can include an acrylic material for casting the elastomeric medication chamber 110 on top of the nozzle plate 102. The mold insert 304 is shown in greater detail in FIG. 3B and can include inserts 306 and 308. As shown in FIG. 3B, the dual compartments 140 and 142 in the agent chamber 110 can be formed by the inserts 306 and 308 respectively in FIG. 3B. In this example, the acrylic mold insert 304 can be computer numerical control (CNC) machined to create the inserts 306 and 308. Alternatively, the assembled mold 300 and/or its components can be fabricated by 3D printing.

In some embodiments, as shown in FIG. 16, the nozzle plate 1602 can be bonded or attached with an adhesive to the bottom side of the agent chamber 1610. In some embodiments, the nozzle plate 1602 can be detachable from the bottom side of the agent chamber 1610, e.g., when the adhesive is reversible.

During use of the nebulizer 100 or 1600 for localized aerosol deposition from a small distance above a target (e.g., a delicate target or surface such as cells), it can be desirable to control: a) the exit velocity of the droplets (e.g., microdroplets) or solid particles to avoid any adverse effect produced on the target (e.g., cells) and/or b) the overall nebulizer output to dispense a precise dose. In some embodiments, the range of exit velocities of the droplets (e.g., microdroplets) or solid particles can be about 1 mm/s to about 100 mm/s. An exemplary approach can rely on precisely timed intermittent actuation of the piezoelectric material, e.g., actuating the piezoelectric element 108 or 1608 with short voltage pulses or duty cycles of the electric signal to the electrodes (130 and 132 in FIGS. 1 and 2A-2B, or 1730 and 1732 in FIG. 17).

Figure 4:
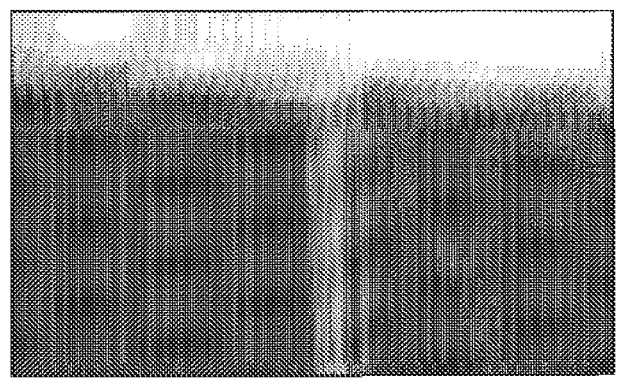
FIG. 4 is an image showing streams of aerosol ejected from an example nebulizer in FIG. 1.

FIG. 4 is an image depicting streams of microdroplets ejected from the nebulizer 100 when actuated continuously at a resonant frequency. In this example, the nebulizer 100 includes a 22 μm metal nozzle plate 102 and a polydimethylsiloxane (PDMS) agent chamber 110. The piezoelectric element 108 is driven continuously at a resonant frequency of approximately 40 kHz with an amplitude of 50 Volts. Any resonant frequency can be used provided that the exit velocity of microdroplets/solid particles does not significantly cause any damage to a target or surface (e.g., cells) and/or a precise dose is provided. For example, the resonant frequency can range from about 20 kHz to about 1 MHz, or from about 30 kHz to about 0.5 MHz. In some examples, the resonant frequency can be about 40 kHz. The resonance can oscillate at an amplitude varying from about 1 V to about 100 V, or from about 10 V to about 75 V, or from about 30V to about 60 V.

The voltage pulses can be generally short, e.g., ranging from picoseconds, to nanoseconds to microseconds to milliseconds. In some examples, a pulse can last for about 0.1 ns to about 500 ms, from about 10 ns to about 100 ms, from about 100 ns to about 10 ms, from about 1 μs to about 1 ms, or from about 5 μs to about 500 μs. Each pulse can be repeated at any rate ranging from nanoseconds to microseconds to milliseconds to seconds. In some example, the pulse can be repeated at a rate of about 0.1 ms to about 10 ms.

Figure 5:
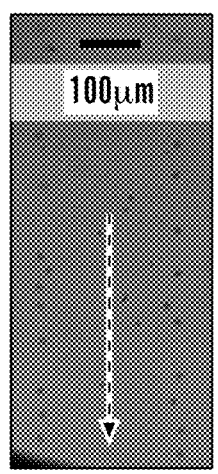
FIG. 5 is high-speed camera image of aerosol exiting nozzles of the example nebulizer in FIG. 1.

FIG. 5 is a high-speed camera image of aerosol exiting nozzles of the example nebulizer 100. The stream of droplets in FIG. 5 can be produced by actuating the piezoelectric element 108 with 10 μs voltage pulses at 50 V amplitude operated at 2.5-ms repetition rate. The resulting droplet velocity is approximately 25 mm/s. Two streams of droplets are visible on both sides of the arrow in FIG. 5. The droplets are approximately 10 μm in size. The spatial separation between the droplets is approximately 50 μm in FIG. 5, which can vary with spatial separation between the nozzles 112 in the plate 102.

Figure 6A:
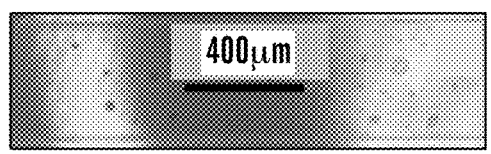
FIG. 6A is an image of a surface prior to deposition of droplets.
Figure 6B:
FIG. 6B is an image showing localized deposition of dyed liquid droplets by the example nebulizer in FIG. 1 on the surface in FIG. 6A.

FIGS. 6A-7D show localized deposition of liquid droplets, magnetic beads, and solid particles into approx. a 400 μm wide and 120 μm deep PDMS microchannel by using one embodiment of the nebulizer described herein, e.g., the nebulizer 100 in FIG. 1. FIG. 6A is an image of a surface prior to deposition of liquid microdroplets. FIG. 6B is an image showing localized deposition of dyed liquid droplets (approx. 10 microns) of different colors onto a surface of a PDMS microchannel. The liquid droplets can be deposited from approx. 10 μm nozzles positioned approximately 320 μm above the bottom of the channel. The deposited droplets can evaporate and coalesce.

Figure 7A:
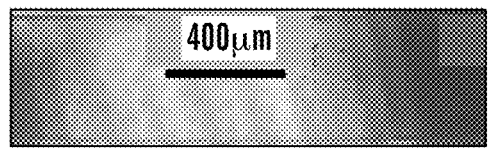
FIG. 7A is an image of a surface prior to localized deposition of solid iron particles.
Figure 7C:
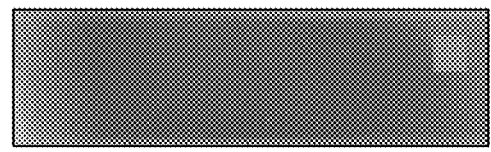
FIG. 7C is an image of a surface prior to localized deposition of magnetic particles.
Figure 7B:
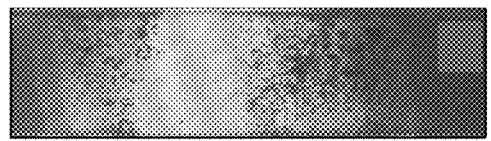
FIG. 7B is an image showing the surface in FIG. 7A after the localized deposition of solid iron particles by the example nebulizer in FIG. 1 on the surface in FIG. 7A.
Figure 7D:
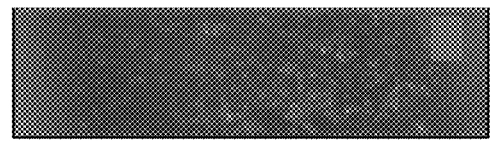
FIG. 7D is an image showing the surface in FIG. 7C after the localized deposition of magnetic particles by the example nebulizer in FIG. 1 on the surface in FIG. 7C.

FIG. 7A is an image of a surface prior to the localized deposition of solid iron particles. FIG. 7B is an image showing the surface in FIG. 7A after the localized deposition of solid iron particles (<9 microns) from dry powder via the nebulizer 100 onto a surface of a PDMS microchannel. The channel in FIG. 7B is 400 μm wide and 120 μm deep. The iron particles can be deposited from approx. 22 μm nozzles positioned approximately 320 μm above the bottom of the channel. FIG. 7C is an image of a surface prior to the localized deposition of magnetic beads. FIG. 7D is an image showing the surface in FIG. 7D after localized deposition of liquid droplets containing 1 μm magnetic beads from a bead suspension via the nebulizer 100 onto a surface of a PDMS microchannel. The image was taken after evaporation of the liquid.

The example nebulizer 100 can be used to expose cells at the air-liquid interface, such as human alveolar or bronchial epithelial cells, to nebulized entities or agents. In accordance with different examples provided herein, nebulized active agents such as, but not limited to, drug or therapeutic agent solutions and suspensions, proteins, peptides, oligonucleotides (e.g., but not limited to, siRNAs and gene vectors), viruses, reagents such as fluorescent dyes, suspensions of solid particles such as quantum dots for fluorescent labeling, cell suspensions or solid particles in a powder form including nanoparticles, can be delivered with the vibrating mesh nebulizer 100 described herein, e.g., the one shown in FIGS. 1-2, positioned a short distance (from hundreds of microns to several millimeters) above the cells cultured at air-liquid interface inside an in vitro cell culture system.

Since the vibrating nozzle plate 102 can be positioned a short distance directly above a target or surface (e.g., cells at the air-liquid interface), a large portion of the generated aerosol (e.g., at least about 40%, at least about 50%, at least about 60%, at least about 70%, at least about 80%, at least about 90%, at least about 95%, at least 98%, or more, of the generated aerosol) can be deposited onto the target or surface (e.g., cells). In some examples, 100% of the generated aerosol can be deposited onto the target or surface (e.g., cells), thus eliminating the costly task of disposing hazardous aerosol that is characteristic for existing exposure systems.

As a result of the high deposition efficiency, establishing the deposited dose can be performed by metering the mass (or volume) of the entity to be nebulized from the agent chamber 110 through the vibrating nozzle plate 102. The residual entity remaining in the agent chamber 110 can be determined and in some cases will be negligible or zero. The residual entity allows making a more accurate determination of dosimetry possible from the agent chamber since the rest of the entity has been deposited. In some examples, the dose can also be established by timing the actuation of the piezoelectric element 108 around the vibrating nozzle plate 102.

The close distance of the nozzle plate 102 from the target or surface (e.g., cells) can allow for delivering different doses of the same entity or agent (e.g., a drug or reagent), or different entities or agents (e.g., drugs or reagents) to different regions of a target surface (e.g., a cell layer at the air-liquid interface). The distance of the nozzle plate 102 from a target such as cells may vary from 50 μm to about 5 cm, from about 100 μm to about 2.5 cm, from about 150 μm to about 1 cm. In some examples, the distance of the nozzle plate 102 from the target (e.g., cells) may be about 300 μm to about 350 μm.

The ability to control the position of each nozzle 112 in the plate 102 can allow for delivery of a microarray of different droplet populations, with different doses and/or types of an entity or agent (e.g., a drug or reagent), to different regions that are spaced across a target surface (e.g., a single cell monolayer). For example, the position of each nozzle 112 in the plate 102 can be adapted to permit deposition of different droplet populations ejected from each respective nozzle onto distinct target areas of a surface (e.g., a single cell monolayer). Thus, in some embodiments, multiple responses of cells to a variety of stimuli can be distinguishably visualized and/or analyzed simultaneously in one cell culture system. In one embodiment, the cell culture system is a microfluidic device with a nebulizer described herein placed above a target surface of a microfluidic channel, wherein the position of each nozzle 112 in the plate 102 can be adapted to permit deposition of different droplet population ejected from each respective nozzle 112 onto distinct target areas of a cell monolayer cultured on the surface of a microfluidic channel. This can effectively make a single channel of a microfluidic device (e.g., an organ-on-a-chip) function like more a multi-well (e.g., 6-well, 12-well, 24-well, 96-well, or more) and thus enable multiplexing (e.g., simultaneous detection of cell responses to multiple stimuli in a single system).

In some embodiments, two or more different entities or agents (e.g., active agents such as cells, e.g., cells of different cell types) can be delivered from different nozzles of the vibrating mesh nebulizer 100 described herein. In some embodiments, cells of different cell types can be delivered from different nozzles of the vibrating mesh nebulizer 100 to create a layer of co-cultured cells, or a very few cells of one cell type such as tumor cells, can be delivered to pre-selected locations on a layer of a different cell type at an air-liquid interface, for example, allowing to study for example early stages of tumor development. The different entities or agents can be delivered at different times, at different quantities and at different velocities.

In some embodiments, the vibrating mesh nebulizer 100 described herein can also be used to generate nano- or micro-particles (e.g., of regular-defined size) for drug or aerosol delivery. For example, the vibrating mesh nebulizer described herein can be used to produce droplets comprising self-assembling molecules (e.g., but not limited to, peptides, proteins, and polynucleotides) and/or polymers (e.g., alginate when mixed with calcium). With the generated droplets, the self-assembling molecules and/or polymers can self-assemble to form nano- or micro-particles.

In some embodiments, the vibrating mesh nebulizer 100 can be used to deposit magnetic or non-magnetic beads (functionalized or non-functionalized) on a target surface, e.g., a surface of a channel in a microfluidic device. In such an application, the nozzle plate 102 may be built either from a non-magnetic metal or a non-metal material such as a polymer. In such an application, the magnetic or non-magnetic beads can be deposited into a microchannel at least partially filled with a fluid (e.g., medium such as cell culture medium or blood). In some embodiments, the vibrating mesh nebulizer 100 can work with fluid on at least one side of the nozzle plate 102 (e.g., one side or both sides of the nozzle plate 102).

The vibration mesh nebulizer 100 may be applied to create microparticles composed of polymers or nanoparticles of a defined size. For example, fabrication of microaggregates of nanoparticles (e.g., stimulus-activated microaggregates such as shear-activated microaggregates, or self-assembling microaggregates (e.g., proteins or polymers)) can be facilitated by aggregation in solution within a droplet of a defined size (e.g., 2-3 μm droplet) ejected from the nozzle(s) of the nebulizer 100 as the droplet passes through air and dries so as to greatly narrow the distribution of particle size. For example, a concentrated solution of nanoparticles can be introduced into the agent chamber 110 of the nebulizer 100. The nebulizer 100 can produce small (a few microns) uniform droplets of the concentrated solutions by aerosolizing the solution of nanoparticles via the nozzle (s) 112. Once the liquid part of the droplet evaporates as it travels through air, an aggregate of nanoparticles (a microaggregate) can be formed. This technique can be used to overcome limitations of current bulk spray-drying techniques, where a wide range of microaggregate dimensions are created due to a broad range of droplet sizes (e.g., ~0.5 μm to ~30 μm). Current methods for production of nanoparticle aggregates, such as spray drying, produce a widely-dispersed population of micro-aggregates due to variability in the droplet production and drying processes. Using a nebulized described herein, e.g., the vibrating nozzle nebulizer 100, uniform droplets can be formed which can in turn result in defined aggregates as the liquid component is evaporated.

Accordingly, in some embodiments, the nebulizer described herein can be used as an alternative for spray drying for any microparticle manufacturing (e.g., drug delivery, aerosol delivery, magnetic particles, dried or liquid foods, such as milk or coffee, etc.). The nebulizer can be scaled to suit a need, e.g., a scale-up to increase the nebulizer output, and used as a stand-alone device or integrated with any system, e.g., a flowing device.

In some embodiments, the nebulizer described herein can be used to produce narrow range particles or particles of regular-defined size in real-time within a flowing device. For example, narrow range particles or particles of regular-defined size can be formed within a flowing device, e.g., a flowing conduit of a device or system, by nebulizing into the flowing device a solution of self-aggregating or self-assembling molecules (e.g., but not limited to, peptides, proteins, polynucleotides, monomers, colloids, polymers) that is loaded into the agent chamber of the nebulizer described herein. Self-assembled particles can form spontaneously or gradually within individual droplets ejected from the nebulizer as the droplets flow within the device or system. In some embodiments, two or more solutions of components of a multi-component gelation system (e.g., but not limited to, fibrinogen and thrombin; or two different polyethylene glycols; chitosan and transglutaminase; or alginate and calcium) can be loaded into separate compartments of the agent chamber. Individual components can become in contact and mix with each other as they get aerosolized through the nozzles, thus forming multi-component particles.

In some embodiments, at least one or more additives (e.g., active agents, e.g., drugs, reagents, surfactants and/or molecule-stabilizing agents) can be further added into a solution to be aerosolized using the nebulizer described herein. For example, one or more active agents such as drugs desired to be encapsulated within the droplets or the resultant particles formed thereafter can be added, e.g., into a solution of self-assembling or self-aggregating molecules (e.g., but not limited to, peptides, proteins, polynucleotides, monomers, colloids, polymers) that is loaded into the agent chamber of the nebulizer.

In some embodiments, any embodiment of a vibrating mesh nebulizer described herein (e.g., similar to the nebulizer 100 in FIG. 1) can be applied to any in vitro cell culture systems, including, but not limited to, cell culture plates or dishes, or microfluidic devices. In such applications, the vibrating mesh nebulizer and methods described herein can be applied to in vitro microfluidic devices, such as organ-on-a-chip devices. Examples of organ-on-a-chip devices that can be used in combination with a vibrating mesh nebulizer can include, but are not limited to, lung-on-a-chip devices described in U.S. application Ser. No. 13/054,095, International Application No. PCT/US12/37096 filed May 9, 2012. Other microfluidic devices that can utilize aerosol delivery of an agent to a target surface (e.g., for coating), or delivery of an active agent to cells or deposition of one cell layer over another for co-culture can also be used with the vibrating mesh nebulizer and methods described herein, for example, microfluidic devices described herein International Application No. PCT/US13/27428 filed Feb. 22, 2013 and entitled "Microfluidic devices for capture of target species;" International Application No. PCT/US12/68725 filed Dec. 10, 2012 and entitled "Integrated human organ-on-chip microphysiological systems" and International Application No. PCT/US12/68766 filed Dec. 10, 2012 and entitled "Organ Chips and Uses Thereof," the contents of which are incorporated herein by reference.

The vibrating mesh nebulizer 100 can be used with in vitro cell culture systems such as Petri dishes, multiwell tissue culture plate, or multiwall tissue culture chamber, e.g., in which the cells are cultured at the air-liquid interface using, for example, Transwell® inserts.

Figure 8A:
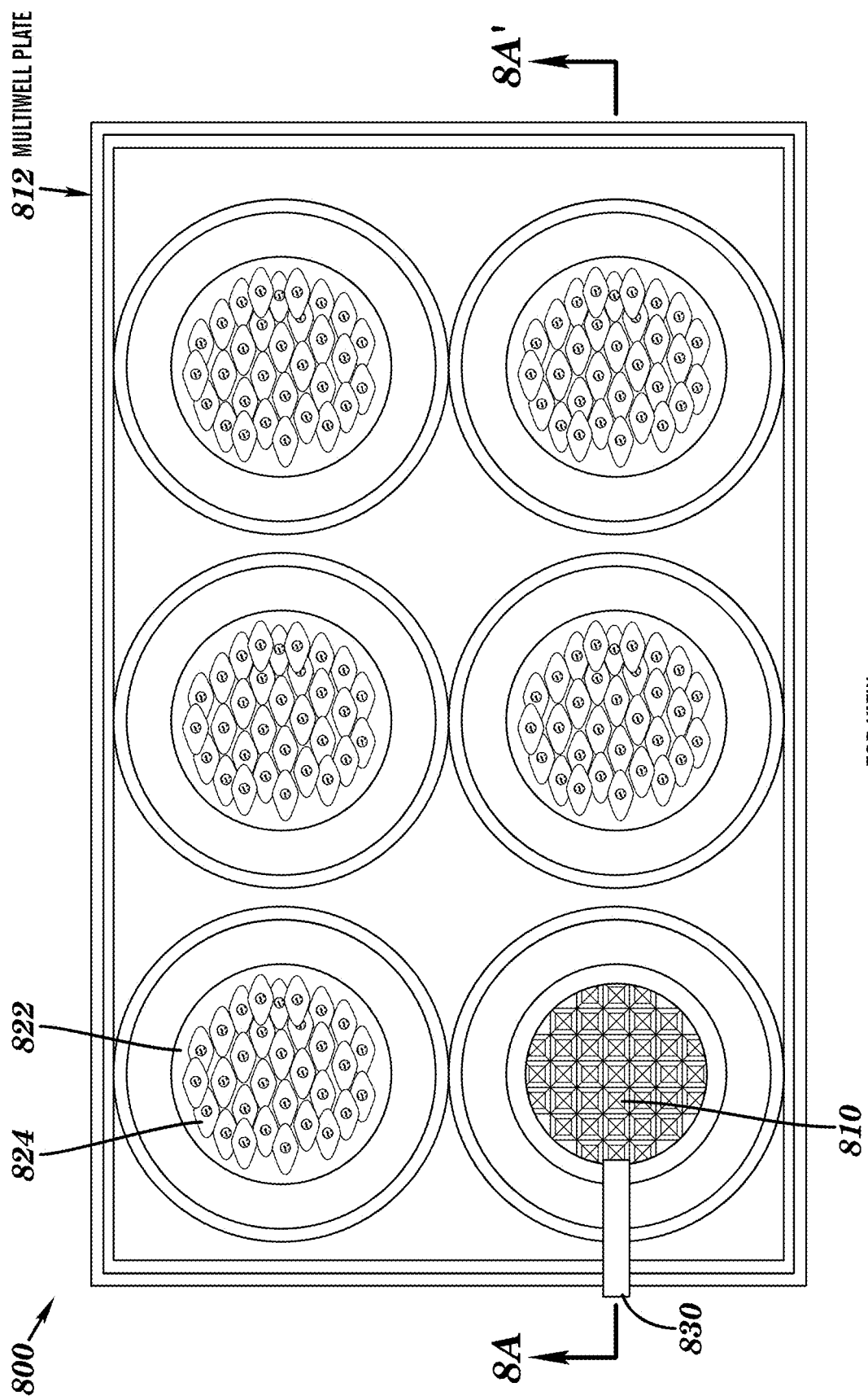
FIG. 8A is a top view of a system for delivering an aerosol to an in vitro cell culture with a single vibrating nozzle plate.
Figure 8B:
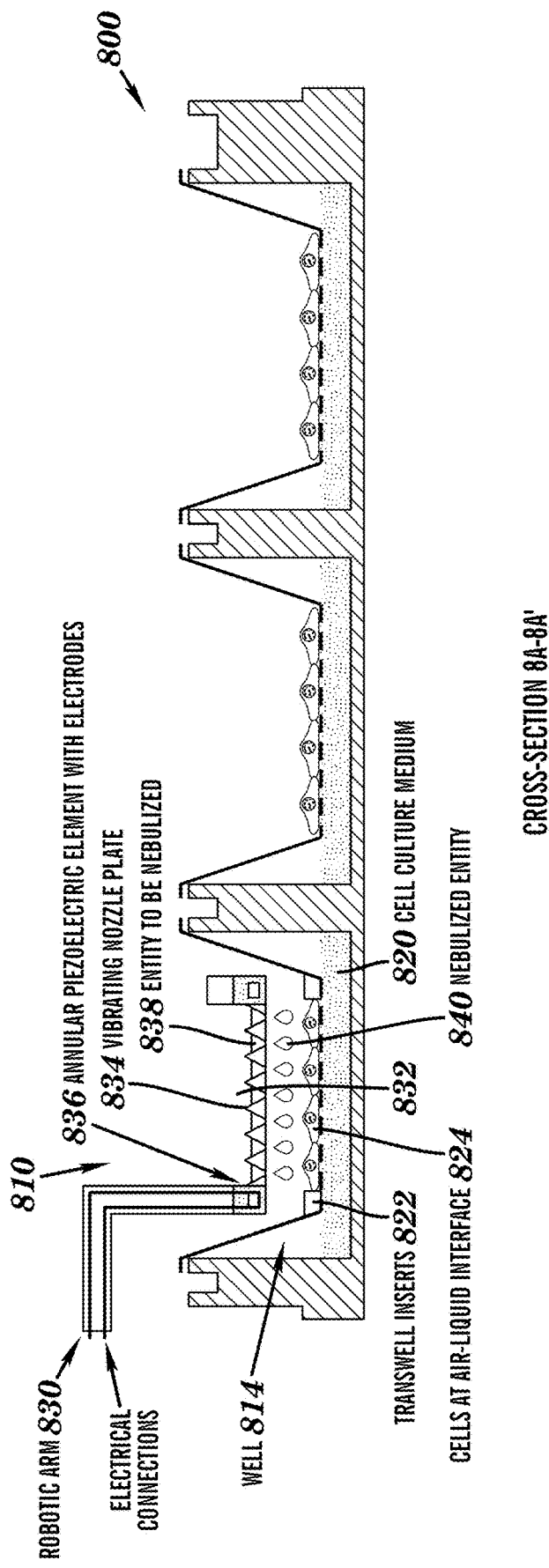
FIG. 8B is a side view of the system in FIG. 8A taken from the line 8A-8A' in FIG. 8A.

Accordingly, the vibrating mesh nebulizer 100 can be adapted for use in different applications and/or with different in vitro cell culture devices. FIG. 8A is a top view of a system 800 to deliver aerosols to in vitro cell cultures with a single vibrating nozzle plate nebulizer 810 which is similar to the nebulizer 100 in FIGS. 1-2. FIG. 8B is a side view of the aerosol delivery system 800 in FIG. 8A taken from the line 8A-8A' in FIG. 8A. The system 800 can include a multi-well plate 812 that includes several wells 814 (e.g., circular wells) for cell culture. In this example, six circular wells 814 are shown, but any number and/or shape of wells can be used. As shown in FIG. 8B, the wells 814 can contain a cell culture medium 820. A Transwell® insert 822 can be used to suspend the cells 824 above the cell culture medium 824

As shown in FIGS. 8A and 8B, aerosol delivery to the in vitro cell cultures 824 at an air-liquid interface can be provided by the nebulizer 810 mounted on a robotic arm 830 which can position the nebulizer over each of the circular wells 814. The nebulizer 810 can include an agent chamber 832 on top of an annular piezoelectric element 836 attached to a vibrating nozzle plate 834. For example, the nebulizer 810 can include an insert forming an agent chamber 832 with a vibrating nozzle plate 834 attached to an annular piezoelectric element 836. The annular piezoelectric element 836 can include electrodes that are powered through wires carried by the robotic arm 830 that can be connected to a power source (not shown). The agent chamber 832 can be filled with an entity 838 by manual or automated dispensing. The filled vibrating nozzle plate 834, mounted on the robotic arm 830, can be automatically or manually positioned a short distance above the cells 824. The piezoelectric element 836 around the nozzle plate 834 can be actuated, resulting in aerosol deposition via nebulization of the entity 840 onto the cells 824. The process can be repeated to deliver aerosol onto the cells in other wells 814. If necessary, the deposition can be performed in a sterile environment, such as a sterile hood. After the deposition, a standard lid can be placed on the multi-well plate 812 and the cells 824 can be incubated in a standard incubator.

Figure 9A:
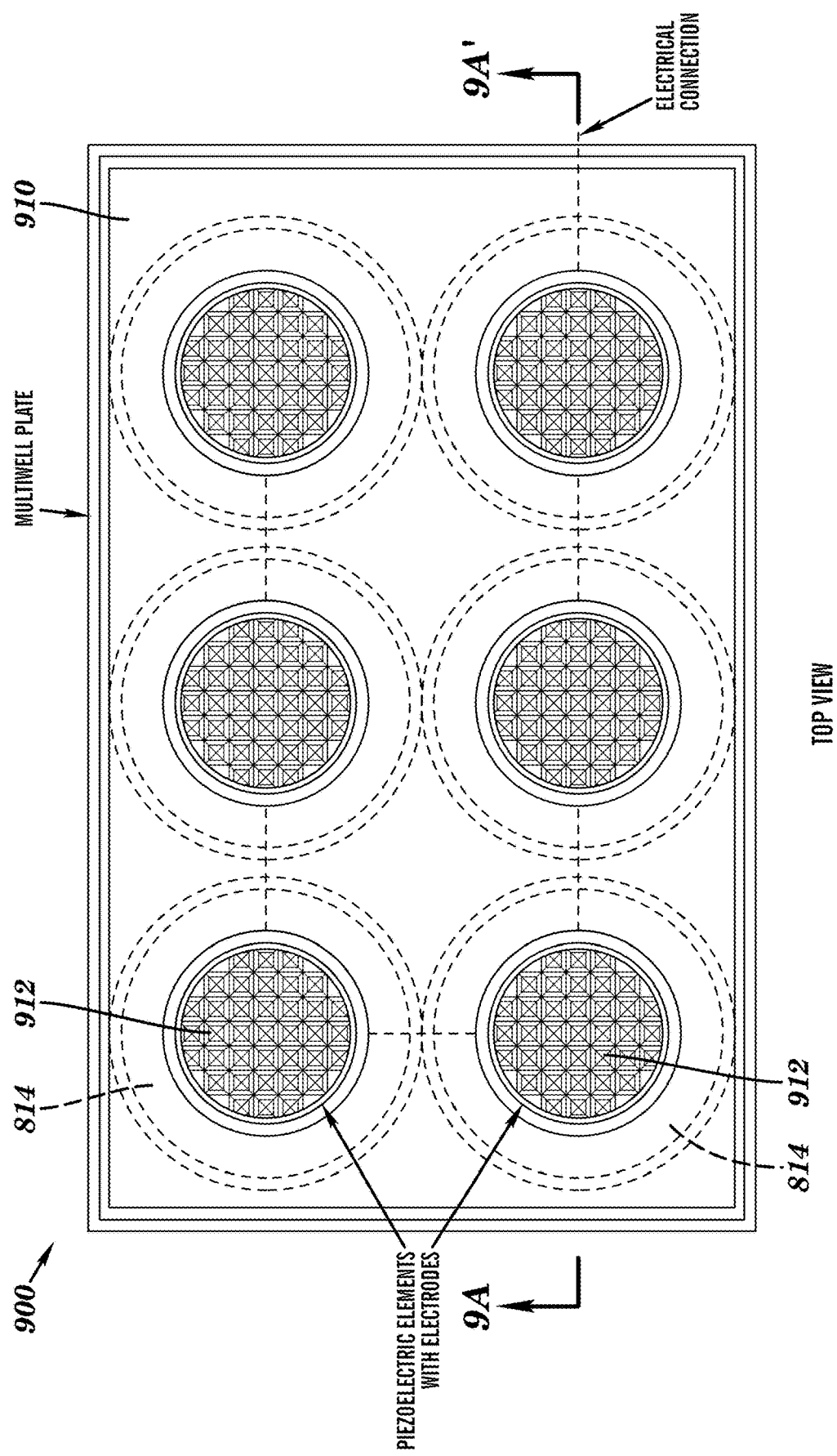
FIG. 9A is a top view of an alternate system to deliver aerosols to in vitro cell cultures via multiple vibrating nozzle plates.
Figure 9B:
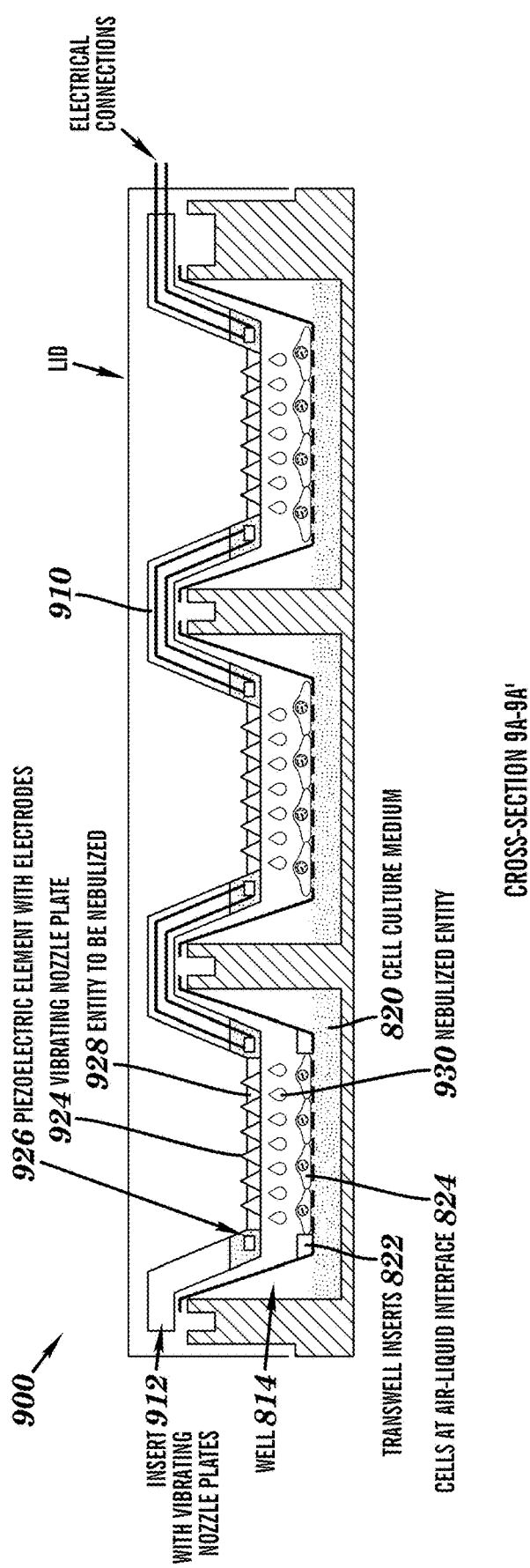
FIG. 9B is a side view of the system in FIG. 9A taken from the line 9A-9A' in FIG. 9A.

FIGS. 9A-9B shown an alternate system 900 to deliver entities to cells cultured in a multi-well plate 812 identical to that in FIGS. 8A-8B. Identical element numbers in FIGS. 8A-8B are used for identical elements in FIGS. 9A-9B. As shown in FIGS. 9A-9B, an inserted nebulizer assembly 910 may be placed on top of the multi-well tissue culture plate 812 containing cells 824 in Transwell® inserts 822. The nebulizer assembly 910 can include multiple nebulizers 912 which are each inserted in a corresponding well 814 (e.g., circular well) on the multi-well plate 812. Each nebulizer 912 formed on the assembly 910 can include an agent chamber 922 on top of an annular piezoelectric element 926 attached to a vibrating nozzle plate 924. For example, the nebulizer 910 can include an insert forming an agent chamber 922 with a vibrating nozzle plate 924 attached to an annular piezoelectric element 926. The agent chamber 922 can be filled with an entity 928 by manual or automated dispensing. As shown in FIG. 9B, the nozzle plate 924 can be positioned a short distance above the cells 824 in the insert 822. The piezoelectric element 926 around the nozzle plate 924 can be actuated, resulting in aerosol deposition via nebulization of the entity 930 onto the cells 824. The annular piezoelectric elements 926 around the vibrating nozzle plates 924 can be electrically interconnected and actuated simultaneously using a single electric power source and thus the entity may be applied simultaneously to the cells 824 in all of the wells 814. Different entities of the same dose or the same entity in different doses can be loaded into different individual agent chambers 922.

Figure 10A:
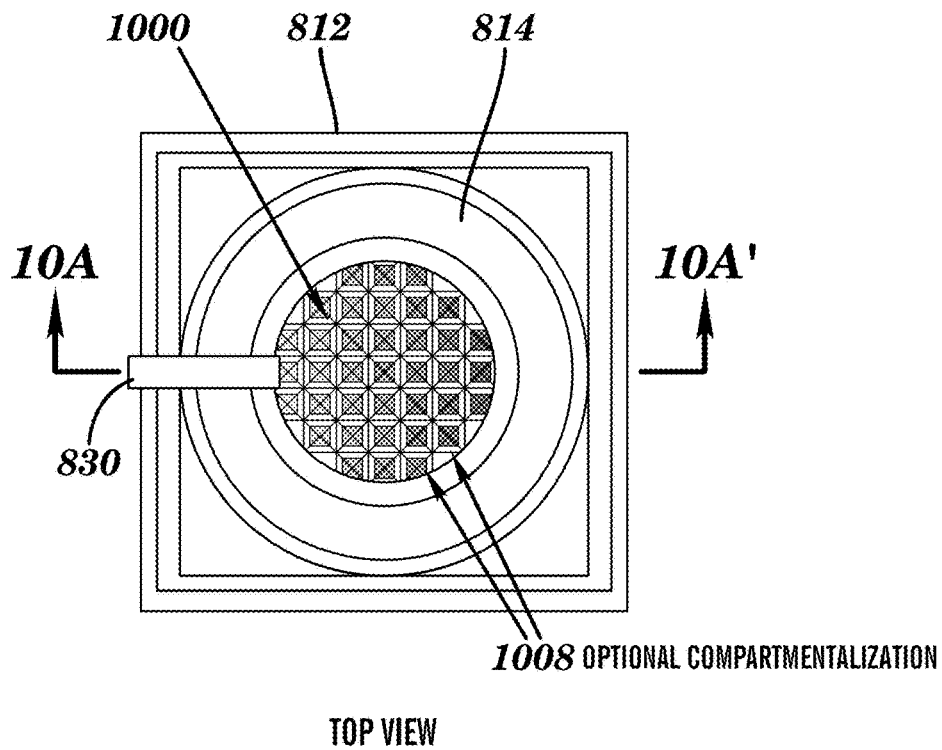
FIG. 10A is a top view of a nebulizer used in the system shown in FIGS. 8A-8B that allows for formation of a concentration gradient by different concentrations of an entity.
Figure 10B:
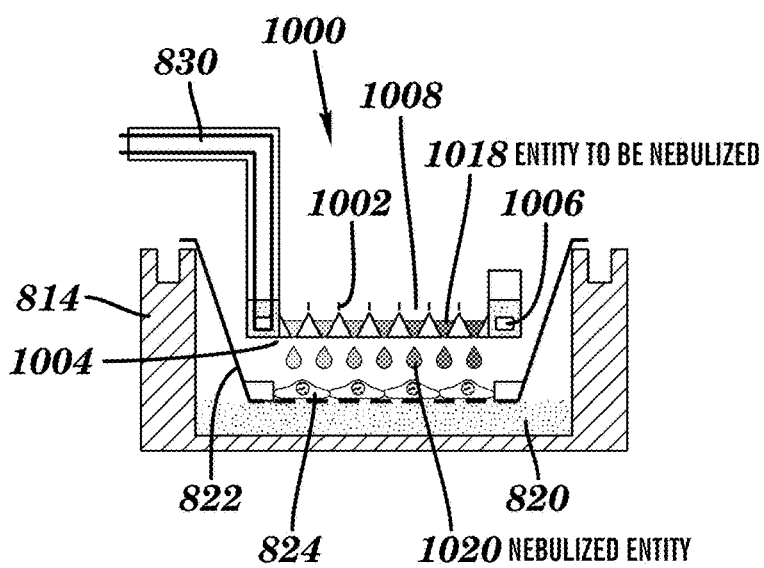
FIG. 10B is a side view of the nebulizer in FIG. 10A taken from the line 10A-10A' in FIG. 10A.

FIG. 10A-10B show a nebulizer 1000 used in the system 800 in FIG. 8A-8B that allows for the formation of a concentration gradient by applications of different concentrations of an entity or agent (e.g., an active agent). Identical element numbers in FIGS. 8A-8B are used for identical elements in FIGS. 10A-10B. As shown in FIGS. 10A and 10B, aerosol delivery to the in vitro cell cultures 824 at an air-liquid interface is accomplished by the nebulizer 1000 mounted on a robotic arm 830 which may position the nebulizer over each of the circular wells 814. The nebulizer 1000 includes an agent chamber 1002 formed by an insert comprising a vibrating nozzle plate 1004 which can be attached to an annular piezoelectric element 1006. The annular piezoelectric element 1006 can include electrodes that are powered through wires carried by the robotic arm 830. In this example, multiple compartments 1008 in the agent chamber 1002 are formed by, e.g., having ridges on the nozzle plate 1004 placed in an insert. Alternatively, multiple compartments 1008 in the agent chamber 1002 can be made when the agent chamber 1002 is fabricated by casting or injection molding from elastomeric materials, e.g., using a similar mold assembly as shown in FIGS. 3A-3B. The compartments 1008 of the agent chamber 1002 can be filled with an entity or agent 1018 by manual or automated dispensing. Then, the filled vibrating nozzle plate 1004, mounted on the robotic arm 830, can be manually or automatically positioned a short distance above the cells 824. The piezoelectric element 1006 around the nozzle plate 1004 can be actuated, resulting in aerosol deposition via nebulization of a reactive agent 1020 onto the cells 824. As shown in FIGS. 10A-10B, the close proximity of the vibrating nozzle plate 1004 to the cells 824 can allow for the formation of a concentration gradient. The concentration gradient can be achieved by loading different concentrations of the reactive agent 1018 to different compartments 1008 formed on top of the vibrating nozzle plate 1004. After nebulization, the concentration gradient of the entity or agent can be formed in the layer of cells 824 at the air-liquid interface.

Figure 10C:
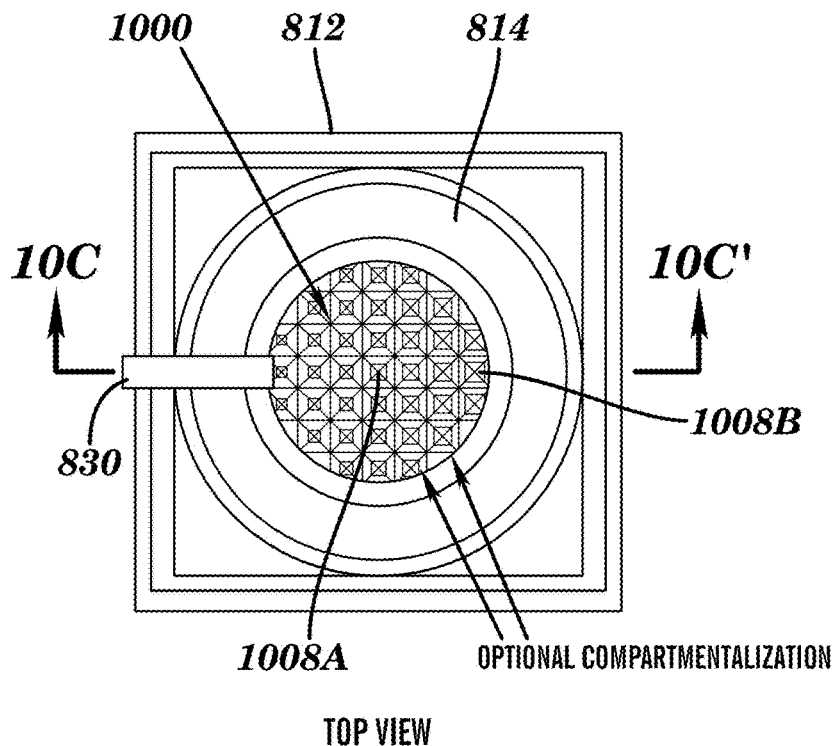
FIG. 10C is a top view of a nebulizer used in the system shown in FIG. 8A-8B that allows for formation of a concentration gradient by different volumes of an entity.
Figure 10D:
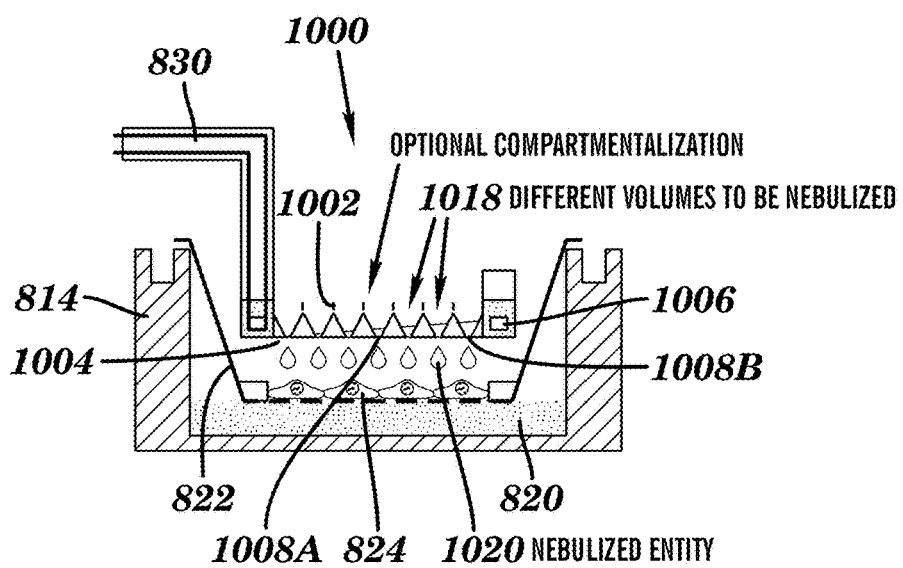
FIG. 10D is a side view of the nebulizer in FIG. 10C taken from the line 10C-10C' in FIG. 10C.

FIG. 10C-10D show the nebulizer 1000 in FIG. 10A-10B used in the system 800 in FIG. 8A-8B that allows for the formation of a concentration gradient by different volumes of an entity or agent. Identical element numbers in FIGS.

8A-8B and 10A-10B are used for identical elements in FIGS. 10C-10D. The compartments such as compartments 1008A and 1008B of the agent chamber 1002 formed by, e.g., ridges on the vibrating nozzle plate 1004 placed in an insert, can be filled with different volumes of the entity or agent 1018 by manual or automated dispensing. The different volumes of the entity or agent create a concentration gradient of the entity or agent 1018 in the layer of cells 824 at the air-liquid interface by nebulization.

Figure 11A:
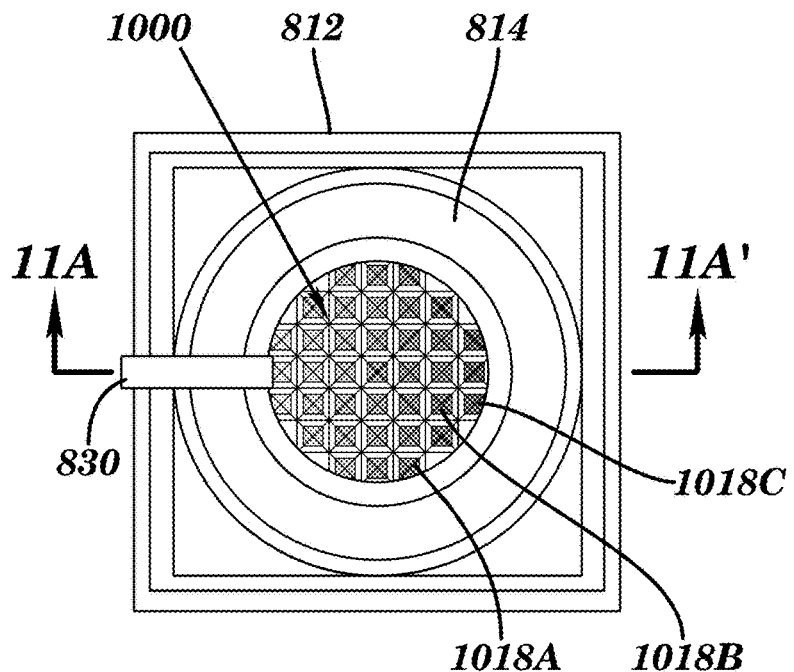
FIG. 11A is a top view of a nebulizer used in the system shown in FIG. 8A-8B that allows for linear patterns of different entities to be deposited.
Figure 11B:
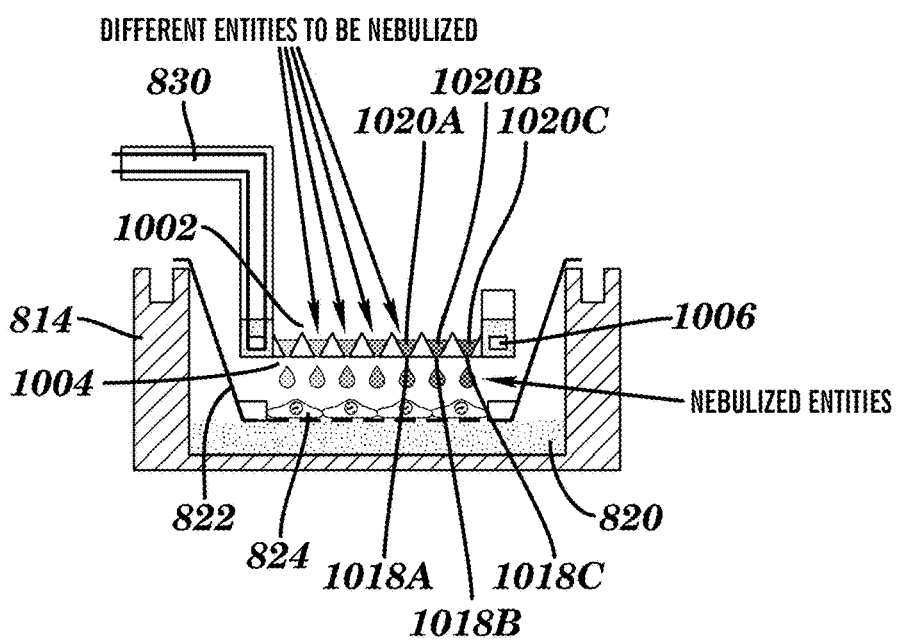
FIG. 11B is a side view of the nebulizer in FIG. 11A taken from the line 11A-11A' in FIG. 11A.

FIG. 11A-10B show the nebulizer 1000 in FIG. 10A-10B used in the system 800 in FIG. 8A-8B that allows for the application of different types of entities to the cells 824. Identical element numbers in FIGS. 8A-8B and 10A-10B are used for identical elements in FIGS. 11A-11B. Compartments such as compartments 1018A, 1018B and 1018C of the agent chamber 1002 formed by, e.g., ridges on the vibrating nozzle plate 1004 placed in an insert, can filled with different entities by manual or automated dispensing. In this example, a first entity 1020A can be filled in compartments 1018A which can be in a linear pattern across the vibration plate 1004. A second entity 1020B can be filled in compartments 1018B which can be arranged linearly next to the compartments 1018A. A third entity 1020C can be filed in compartments 1018C which can be arranged linearly next to the compartments 1018B. Any number of different entities can be used in different linear or pre-determined patterns of compartments. In this example, the different entities 1020A-1020C (e.g., active agents) can be loaded into different compartments of the vibrating nozzle plate 104 and nebulized. In this example, linear patterns of entities can be deposited into the layer of cells 824 at the air-liquid interface.

Figure 11C:
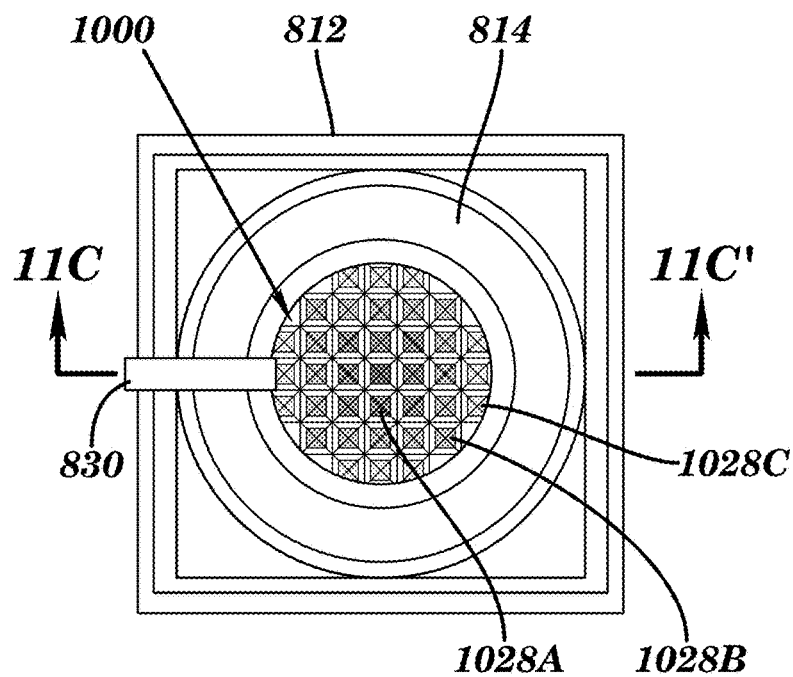
FIG. 11C is a top view of a nebulizer used in the system shown in FIG. 8A-8B that allows for concentric patterns of different entities to be deposited.
Figure 11D:
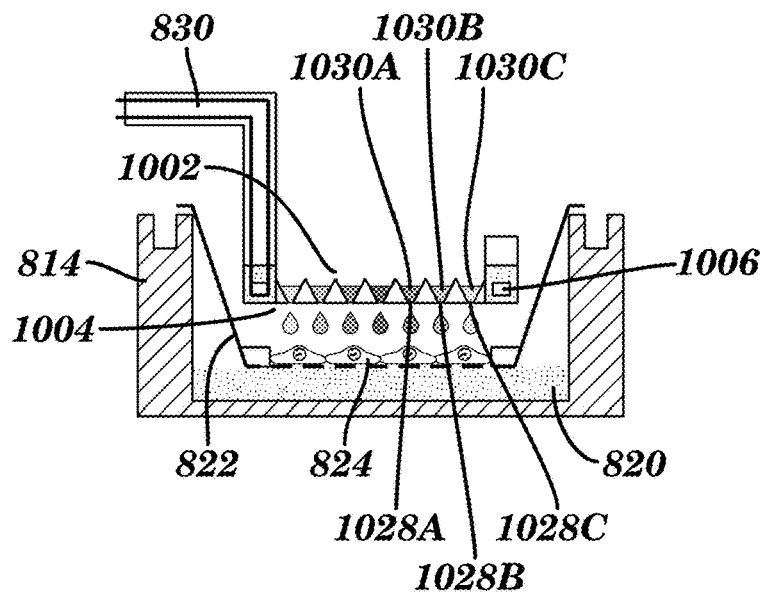
FIG. 11D is a side view of the nebulizer in FIG. 11C taken from the line 11C-11C' in FIG. 11C.

FIG. 11C-11D show the nebulizer 1000 in FIG. 10A-10B used in the system 800 in FIG. 8A-8B that allows for the application of different types of entities to the cells 824. Identical element numbers in FIGS. 8A-8B and 10A-10B are used for identical elements in FIGS. 11C-11D. Compartments such as compartments 1028A, 1028B and 1028C of the agent chamber 1002 formed, e.g., by ridges on the vibrating nozzle plate 1004 placed in an insert, are filled with different entities by manual or automated dispensing. In this example, a first entity 1030A can be filled in compartments 1028A which can be in a concentric pattern in the center compartments of the vibration plate 1004. A second entity 1030B can be filed in compartments 1028B which can be arranged concentrically around the compartments 1028A. A third entity 1030C can be filed in compartments 1028C which can be arranged concentrically around the compartments 1028B. Any number of different entities may be used in different concentric patterns of compartments. In this example, the different entities 1030A-1030C (e.g., active agents) can be loaded into different compartments of the vibrating nozzle plate 104 and nebulized. In this example, concentric patterns of entities can be deposited into the layer of cells 824 at the air-liquid interface.

Figure 12A:
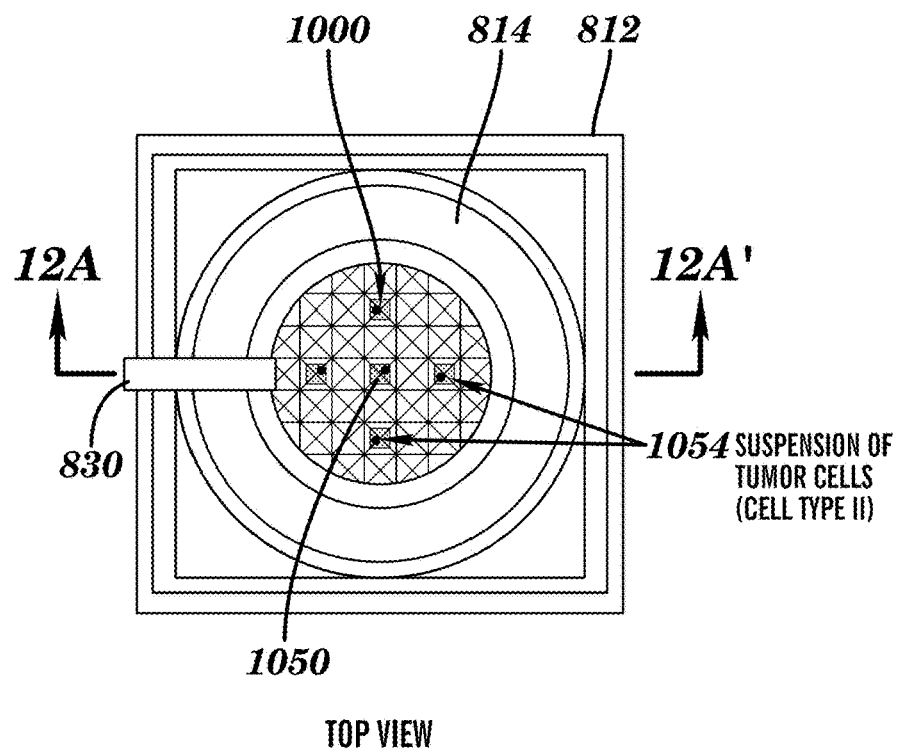
FIG. 12A is a top view of a nebulizer used in the system shown in FIG. 8A-8B that allows different sized nozzles to seed cells at predetermined locations.
Figure 12B:
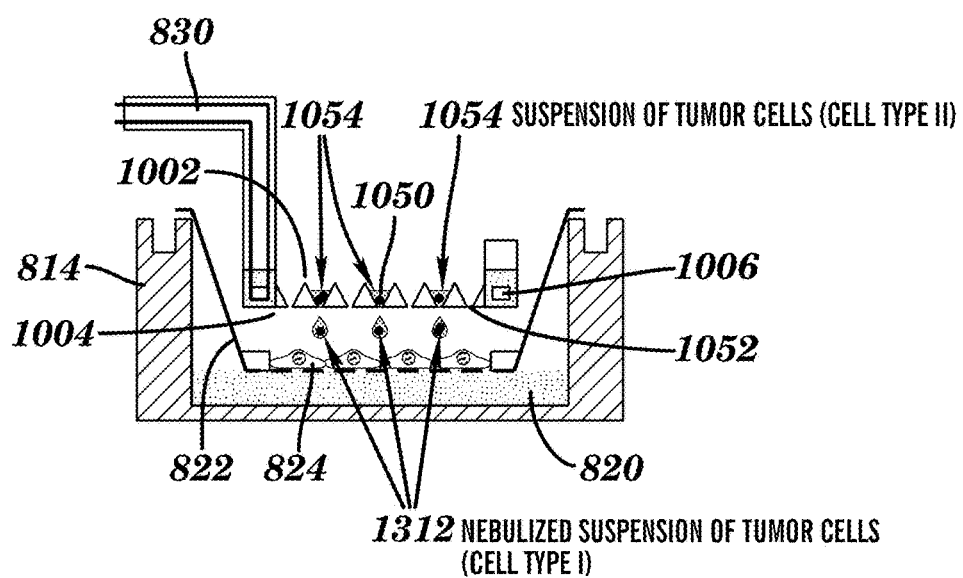
FIG. 12B is a side view of the nebulizer in FIG. 12A taken from the line 12A-12A' in FIG. 12A.

In another example, selected compartments of the vibrating nozzle plate may be furnished with nozzles of a larger size and may be loaded with a cell suspension. FIG. 12A is a top view of the nebulizer 1000 used in the system 800 shown in FIG. 8A-8B that allows different sized nozzles to seed cells at predetermined locations. FIG. 12B is a side view of the nebulizer 1000 in FIG. 12A taken from the line 12A-12A' in FIG. 12A. Identical element numbers in FIGS. 8A-8B and 10A-10B are used for identical elements in FIGS. 12A-12B. The vibrating plate 1004 can include selected compartments 1050 which form larger nozzles 1052. In this example, tumor cells 1054 can be placed in the selected compartment 1050 for nebulization to be suspended or co-cultured with certain cells 824. Nebulizing the cell suspension can result in seeding the cells 824 in predefined locations. An example of an application is seeding a low number of tumor cells 1054 on a cell layer 824 of another type to study early stages of tumor development. However, this technique can also be applied to any co-culture model.

As shown in FIGS. 13A and 13B, localized aerosol delivery can be accomplished with a single nozzle nebulizer 1300 in the cells 824 in the system 800 in FIG. 8A-8B. Identical element numbers in FIGS. 8A-8B are used for identical elements in FIGS. 13A-13B. The nebulizer 1300 is mounted on a robotic arm 830 which can position the nebulizer over each of the individual cells 824 in the well 814 (e.g., a circular well). The nebulizer 1300 can include an agent chamber 1302 on top of an annular piezoelectric element 1306 attached to a vibrating nozzle plate 1304. The annular piezoelectric element 1306 can include electrodes that are powered through wires carried by the robotic arm 830. The agent chamber 1302 can be filled with an entity 1310 by manual or automated dispensing. The nozzle plate 1304 comprises a single nozzle 1312 which can be approximately the diameter of a specific cell 824. The single nozzle 1312 can be manually or automatically positioned a short distance above the cells 824 by the robotic arm 830. The piezoelectric element 1306 around the nozzle plate 1304 can be actuated, resulting in aerosol deposition via nebulization of the entity 1314 onto the cells 824. By moving the nozzle plate 1304, combined with actuating the piezoelectric element 1306 around the nozzle plate 1304, the nebulized entity 1314 can be delivered to a desired single location or multiple locations.

Figure 14A:
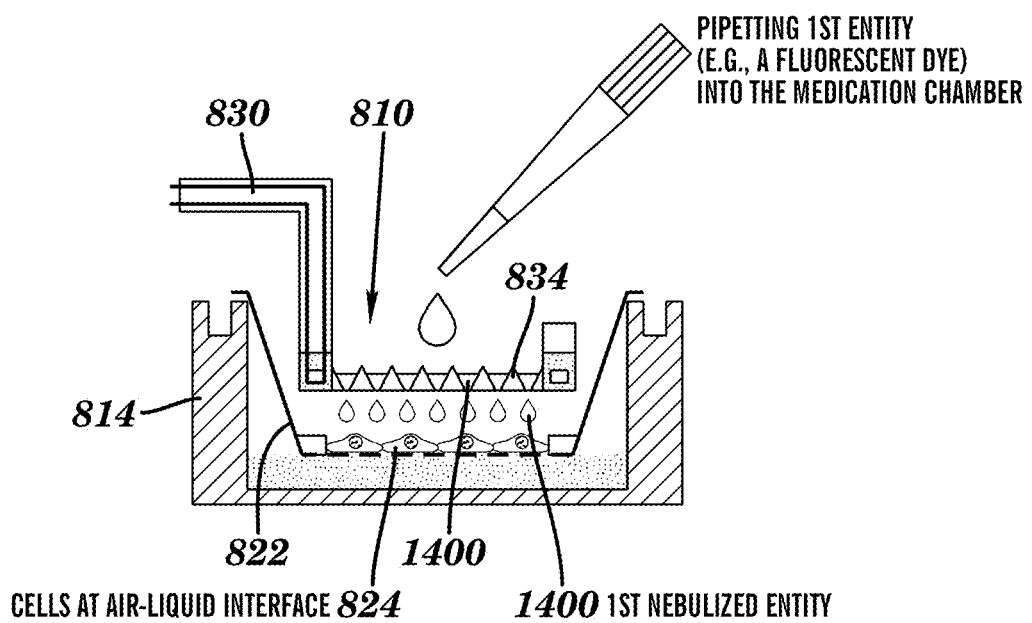
FIGS. 14A-14B are schematic diagrams showing sequential deposition of multiple entities over a layer of cells at the air liquid interface using the nebulizer in FIG. 8A-8B.
Figure 14B:
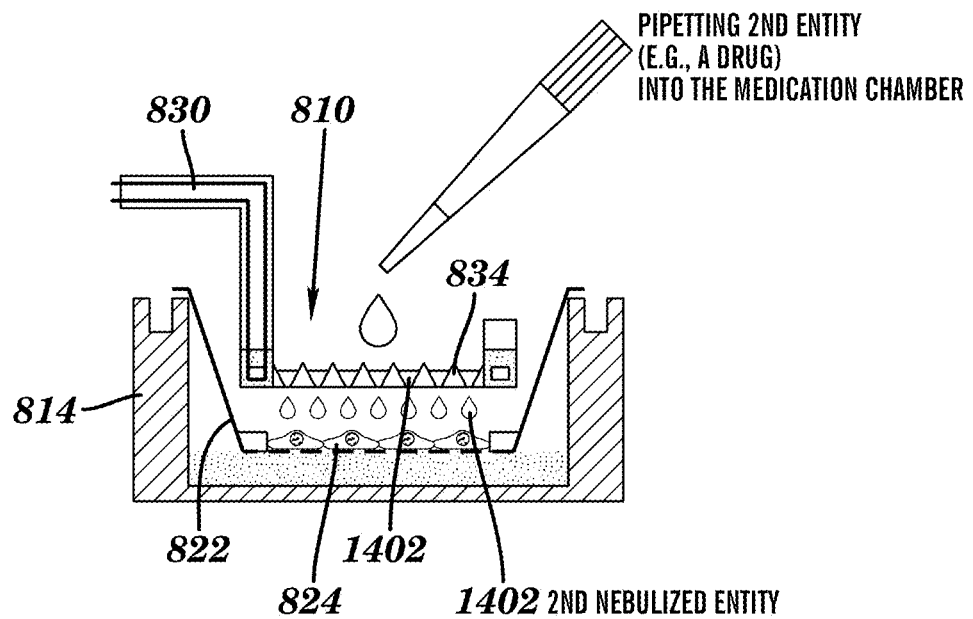

In another example, the nebulizer 810 in FIGS. 8A-8B can used for sequential deposition multiple entities into a layer of cells at the air liquid interface. As shown in FIG. 14A, a first entity 1400 can be applied using the nebulizer 810. After nebulizing the first entity, the vibrating nozzle plate 834, connected to the robotic arm 830, can be moved outside the well 814 and a rinse solution can be dispensed into the nozzle plate 834 and nebulized. This can be followed by dispensing a second entity 1402 into the nozzle plate 834, moving it above the cells 824 as shown in FIG. 14B and nebulizing the second entity 1402 onto the cells 824 at the air-liquid interface.

FIG. 16 is a schematic diagram depicting how a rigid body motion nebulizer 1600 comprising a rigid piezoelectric element 1608 can be used in dispensing aerosolized chemical and/or biological entities to an array of in vitro cell culture devices such as an array of microfluidic devices (e.g., organs-on-chips) 1605. The nebulizer assembly 1600 can be attached to an X-Y-Z positioning system 1601, such as a robotic arm (not shown). The robotic arm can be capable of actuating the agent chamber clamping mechanism using an auxiliary motor. The arm can be programmed to select and clamp one of the disposable agent chambers 1610 from the storage bay 1603. The agent chambers can contain any agent desired to be nebulized or deposited, e.g., but not limited to, biological molecules such as proteins or peptides (e.g., extracellular matrix molecules), or a cell suspension; chemical molecules, e.g., a fluorescent dye; drug or therapeutic agent solution or powder; solid particles (e.g., magnetic particles); or any combinations thereof. Agent chambers 1610 can be sealed at the top with a covering or protection sheet (e.g., a thin aluminum foil or similar film), e.g., to facilitate storage by minimizing evaporation and reducing a possibility of contamination. The seal can be pierced with a piecing point on the robotic arm prior to clamping. Piecing point can be disposable, suppressing a possibility of cross-contamination. After clamping an agent chamber 1610, a nebulized entity can be delivered to selected microfluidic devices (e.g., organs-on-chips) 1605 by moving the agent chamber 1610 above the cell culture areas while vibrations are transmitted to the agent chamber 1610. The beam vibrations can be generated by applying voltage pulses of appropriate amplitude, frequency and duration to the beam (piezoelectric element). When the nebulizer is properly calibrated, the voltage waveform can be chosen such that a precise number of droplets is generated, down to a single droplet from each nozzle per individual excitation (on-demand droplet generation). Initially, the piezoelectric elements can be used to excite vibrations in the beam 1608 and agent chamber 1610; to arrest the beam vibrations after the desired number of droplets have been released, the piezoelectric elements can be actuated out of phase with the vibrations to dampen them out. During deposition of aerosolized entities nozzle of plate of the agent chamber 1610 can be positioned a short distance above target area, ensuring high deposition efficiency and allowing for localized deposition. Low residual loss of biological or chemical entity in the agent chamber 1610 can be controlled by choosing proper geometry and surface properties of the inner walls of the agent chamber and the nozzle plate. Stiffness of the nozzle plate can be controlled by its thickness and its structural features. Apparent stiffness of the plate can be increased by decreasing the diameter of the agent chamber. FIG. 16 depicts an embodiment with a round footprint of the agent chamber. However, the footprint can be also elongated with a long and narrow array of nozzles. This can be desirable for scanning over elongated areas. Additionally, an elongated geometry of the nozzle plate can provide higher apparent stiffness.

After a precise amount of chemical or biological entity is delivered in an on-demand fashion from a short distance to selected microfluidic devices (e.g., organs-on-chips) 1605, the robotic arm can return the agent chamber 1610 to the storage bay 1603. This process can be repeated by selecting a different agent chamber 1610 from the storage bay 1603 and sequentially delivering its contents to the same or different microfluidic devices (e.g., organs-on-chips) 1605. Different agent chambers 1610 can contain different entities and/or quantities of entities and can have different numbers and sizes of nozzles. In one embodiment, deposition of an aerosolized extracellular matrix protein to cell scaffolds can be followed, for example, by deposition of cells from a cell suspension, or deposition of an aerosolized drug to cells at air-liquid interface can be followed by deposition an aerosolized fluorescent dye. Because agent chambers 1610 are disposable, the possibility of cross-contamination is reduced.

Embodiments of various aspects described herein can be defined in any of the following numbered paragraphs:
1. A system for aerosol delivery of an entity, the system comprising:
 a nebulizer including
 a chamber to hold a dose of the entity,
 a nozzle plate including at least one nozzle, and
 a piezoelectric element coupled to the nozzle plate; and
 a power source coupled to the piezoelectric element, the power source, when activated, energizing the piezoelectric element to vibrate the nozzle plate to cause the dose of the entity to be nebulized through the nozzle in a predefined direction.
2. The system of paragraph 1, wherein the piezoelectric element includes an annular ring and the chamber is formed by the piezoelectric element and the nozzle plate.
3. The system of paragraph 1 or 2, wherein the chamber includes a plurality of compartments to hold the entity.
4. The system of paragraph 3, wherein the chamber is molded from an elastomeric material.
5. The system of any of paragraphs 1-4, further comprising a target surface and wherein the at least one nozzle directs the nebulized entity onto the target surface.
6. The system of paragraph 5, further comprising a layer of cells in vitro supported by the target surface, wherein the nebulized entity can be applied to the layer of cells.
7. The system of paragraph 6, wherein the layer of cells are cells in microfluidic channel.
8. The system of any of paragraphs 5-7, wherein the proximity of the nebulizer to the target surface is selected to disburse over 40% of the entity when the entity is nebulized.
9. The system of any of paragraphs 1-8, wherein the nozzle plate includes a plurality of nozzles.
10. The system of any of paragraphs 1-9, wherein the nozzle has a diameter selected to form a microdroplet having a selected size of the entity when the entity is nebulized.
11. The system of any of paragraphs 1-10, wherein the piezoelectric element is a piezoceramic material.
12. The system of any of paragraphs 1-11, wherein the piezoelectric element is mounted on a first surface of a polymeric film and a patterned electrode layer is formed on the first surface of the polymeric film, and the patterned electrode layer is adapted to be coupled to the power source to provide power to the piezoelectric element.
13. The system of any of paragraphs 1-12, wherein the power source is capable of being controlled to provide energy pulses at, at least one of, a predetermined frequency, amplitude or duration, to activate the piezoelectric element to control the nebulization of the entity.
14. A method for aerosol delivery of an entity to a target surface, the method comprising:
 positioning a nebulizer in close proximity to the target surface, the nebulizer including a chamber to hold the entity; a nozzle plate including at least one nozzle and a piezoelectric element coupled to the nozzle plate; and
 energizing the piezoelectric element to vibrate the nozzle plate and cause the entity to be nebulized through the nozzle forming an aerosol that is applied to the target surface.
15. The method of paragraph 14, further comprising dispensing a dose of the entity into the chamber of a nebulizer.
16. A system for providing a nebulized entity to a cell in an in vitro culture system, the system comprising:
 a plate including at least one well;
 an insert holding cells, the insert suspended in the well;
 a nebulizer in close proximity to the insert, the nebulizer including a chamber adapted to hold the entity, a nozzle plate including at least one nozzle, and a piezoelectric element coupled to the nozzle plate; and
 a power source coupled to the piezoelectric element, the power source, when activated, energizing the piezoelectric element to vibrate the nozzle plate and cause the entity to be nebulized through the nozzle forming an aerosol that is applied cells in the insert.
17. The system of paragraph 16, wherein the plate includes a plurality of wells and a plurality of inserts holding cells.
18. The system of paragraph 16 or 17, further comprising a robotic arm connected to the nebulizer, wherein the robotic arm can position the nebulizer over at least two regions within said at least one well in sequence to apply the entity to the cells at said at least two regions within the well.

19. The system of paragraph 16 or 17, further comprising a robotic arm connected to the nebulizer, wherein the robotic arm can position the nebulizer over at least two of the plurality of wells in sequence to apply the entity to the cells in at least two of the plurality of wells.
20. The system of any of paragraphs 16-19, wherein the chamber includes multiple compartments for the entity.
21. The system of paragraph 20, wherein the entity is filled into one of the compartments and a second entity is filled into another one of the compartments.
22. The system of paragraph 20 or 21, wherein a concentration gradient of the entity applied to the cells can be established by either changing the volume of the entity in the multiple compartments or the concentration of the entity in the multiple compartments.
23. A system for delivering a nebulized entity into a microfluidic device, the system comprising:
  at least one microfluidic device comprising a channel;
  a nebulizer in close proximity to the channel, the nebulizer including a chamber adapted to hold the entity, a nozzle plate including at least one nozzle, and a piezoelectric element capable of coupling to the nozzle plate; and
  a power source coupled to the piezoelectric element, the power source, when activated, energizing the piezoelectric element to vibrate the nozzle plate and cause the entity to be nebulized through the nozzle forming an aerosol that is delivered to the channel of the microfluidic device.
24. The system of paragraph 23, wherein a bottom surface of the channel comprises cells cultured thereon, and the aerosol is applied to the cells.
25. The system of paragraph 24, wherein the bottom surface of the channel is porous.
26. The system of paragraph 25, wherein the bottom surface of the channel comprises a porous membrane.
27. The system of any of paragraphs 23-26, wherein said at least one microfluidic device is an organ-on-a-chip device.
28. The system of any of paragraphs 23-27, wherein the nebulizer is adapted to be integrated with a top surface of the channel of the microfluidic device.
29. The system of paragraph 28, wherein the top surface of the channel adapted to be integrated with the nebulizer is removable.
30. The system of any of paragraphs 23-29, wherein at least the chamber and the nozzle plate forming the bottom end of said at least the chamber is removable from the piezoelectric element of the nebulizer.
31. The system of any of paragraphs 23-30, further comprising a robotic arm connected to the nebulizer.
32. The system of paragraph 31, wherein the robotic arm can position the nebulizer over at least a portion of the channel of said at least one microfluidic device.
33. The system of paragraph 31 or 32, wherein the robotic arm can position the nebulizer over at least two channels within the same microfluidic device in sequence for delivery of the entity.
34. The system of any of paragraphs 31-33, wherein the robotic arm can position the nebulizer over a first channel of a first microfluidic device and a second channel of a second microfluidic device in sequence for delivery of the entity to said at least two microfluidic devices.
35. The system of any of paragraphs 23-34, wherein the chamber includes multiple compartments for the entity.
36. The system of paragraph 35, wherein the entity is filled into one of the compartments and a second entity is filled into another one of the compartments.
37. The system of paragraph 35 or 36, wherein a concentration gradient of the entity can be established by either changing the volume of the entity in the multiple compartments or the concentration of the entity in the multiple compartments.
38. The system of any of paragraphs 23-37, wherein the nozzle plate comprises a plurality of the nozzles.
39. The system of paragraph 38, wherein the positions of the plurality of the nozzles are configured to permit deposition of the entity and the second entity onto spatially-distinct areas of the channel.

SOME SELECTED DEFINITIONS

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

As used herein the term "comprising" or "comprises" is used in reference to compositions, methods, and respective component(s) thereof, that are essential to the invention, yet open to the inclusion of unspecified elements, whether essential or not.

The singular terms "a," "an," and "the" include plural referents unless context clearly indicates otherwise. Similarly, the word "or" is intended to include "and" unless the context clearly indicates otherwise.

Other than in the operating examples, or where otherwise indicated, all numbers expressing quantities of ingredients or reaction conditions used herein should be understood as modified in all instances by the term "about." The term "about" when used in connection with percentages may mean±5% of the value being referred to. For example, about 100 means from 95 to 105.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

As used herein, the terms "proteins" and "peptides" are used interchangeably herein to designate a series of amino acid residues connected to the other by peptide bonds between the alpha-amino and carboxy groups of adjacent residues. The terms "protein", and "peptide", which are used interchangeably herein, refer to a polymer of protein amino acids, including modified amino acids (e.g., phosphorylated, glycated, etc.) and amino acid analogs, regardless of its size or function. Although "protein" is often used in reference to relatively large polypeptides, and "peptide" is often used in reference to small polypeptides, usage of these terms in the art overlaps and varies. The term "peptide" as used herein refers to peptides, polypeptides, proteins and fragments of proteins, unless otherwise noted. The terms "protein" and "peptide" are used interchangeably herein when referring to a gene product and fragments thereof. Thus, exemplary peptides or proteins include gene products, naturally occurring proteins, homologs, orthologs, paralogs, fragments and other equivalents, variants, fragments, and analogs of the foregoing.

The term "statistically significant" or "significantly" refers to statistical significance and generally means at least two standard deviation (2SD) away from a reference level. The term refers to statistical evidence that there is a difference. It is defined as the probability of making a decision to reject the null hypothesis when the null hypothesis is actually true.

As used interchangeably herein, the terms "essentially" and "substantially" means a proportion of at least about 60%, or preferably at least about 70% or at least about 80%, or at least about 90%, at least about 95%, at least about 97% or at least about 99% or more, or any integer between 70% and 100%. In some embodiments, the term "essentially" means a proportion of at least about 90%, at least about 95%, at least about 98%, at least about 99% or more, or any integer between 90% and 100%. In some embodiments, the term "essentially" can include 100%.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated may be further modified to incorporate features shown in any of the other embodiments disclosed herein.

What is claimed is:

1. A microfluidic device for monitoring a biological function, the microfluidic device comprising i) a channel, said channel comprising a top surface, and ii) a nebulizer integrated with said top surface of the channel, the nebulizer including a piezoelectric element and a rigid nozzle plate having a plurality of nozzles spaced apart across the channel.

2. The microfluidic device of claim 1, wherein the piezoelectric element is capable of detachably coupling to the nozzle plate.

3. The microfluidic device of claim 1, wherein the channel comprises cells therein, and the nebulizer can be applied to at least a portion of the cells.

4. The microfluidic device of claim 1, wherein the channel is formed by at least one elastomeric material.

5. The microfluidic device of claim 1, further comprising a power source coupled to the piezoelectric element.

6. The microfluidic device of claim 5, wherein the power source is capable of being controlled to provide energy pulses at, at least one of, a predetermined frequency, amplitude or duration, to activate the piezoelectric element to control the nebulizer.

7. The microfluidic device of claim 1, wherein the piezoelectric element is mounted on a first surface of a polymeric film and a patterned electrode layer is formed on the first surface of the polymeric film, the patterned electrode layer being adapted to be coupled to the power source to provide power to the piezoelectric element.

8. The microfluidic device of claim 1, wherein the plurality of nozzles is configured to deliver a microarray of different droplet populations.

9. A method, comprising:
a) providing cells and a microfluidic device comprising i) a channel, said channel comprising a top surface, and ii) a nebulizer integrated with said top surface of placed above the channel, the nebulizer including a piezoelectric element and a rigid nozzle plate having a plurality of nozzles spaced apart across the channel;
b) introducing said cells into said channel below said nebulizer; and
c) actuating said piezoelectric element so as to deposit an aerosol onto the cells.

* * * * *